US008451452B2

(12) United States Patent
Podoleanu et al.

(10) Patent No.: US 8,451,452 B2
(45) Date of Patent: May 28, 2013

(54) METHOD FOR DEPTH RESOLVED WAVEFRONT SENSING, DEPTH RESOLVED WAVEFRONT SENSORS AND METHOD AND APPARATUS FOR OPTICAL IMAGING

(76) Inventors: Adrian Podoleanu, Canterbury (GB); Simon Tuohy, Oxford (GB)

( * ) Notice: Subject to any disclaimer, the term of this patent is extended or adjusted under 35 U.S.C. 154(b) by 486 days.

(21) Appl. No.: 12/764,510

(22) Filed: Apr. 21, 2010

(65) Prior Publication Data

US 2011/0134436 A1    Jun. 9, 2011

(30) Foreign Application Priority Data

Apr. 29, 2009  (GB) .................... 0907277.8
Jul. 2, 2009    (GB) .................... 0911441.4

(51) Int. Cl.
*G01B 9/02*        (2006.01)
*G01B 11/02*      (2006.01)

(52) U.S. Cl.
USPC ............................ 356/479; 356/497; 351/221

(58) Field of Classification Search
USPC .................. 356/496–516, 479; 351/221
See application file for complete search history.

(56) References Cited

U.S. PATENT DOCUMENTS

| 5,633,715 A * | 5/1997 | Ai et al. ....................... 356/497 |
| 2006/0033933 A1* | 2/2006 | Feierabend et al. .......... 356/512 |
| 2007/0046948 A1* | 3/2007 | Podoleanu et al. ........... 356/497 |
| 2008/0281303 A1* | 11/2008 | Culbertson et al. ............... 606/5 |

OTHER PUBLICATIONS

Laubscher, et al., Video-rate three-dimensional optical coherence tomography, Optics Express, May 6, 2002, vol. 10, No. 9, p. 429-435.*
Moon, et al. "Ultra-high-speed optical coherence tomography with a stretched pulse supercontinuum source", Optics Express, 2006, vol. 14, pp. 11575-11584.*
Fernandez, et al, "Ocular aberrations as a function of wavelength in the near infrared measured with a femtosecond laser," Optics Express 13, 400-409 (2005).*
Hermann, et al, "Adaptive-optics ultrahigh-resolution optical coherence tomography", Optics Letters, vol. 28, No. 18, 2004, 2142-2144.*

* cited by examiner

*Primary Examiner* — Gregory J Toatley
*Assistant Examiner* — Dominic J Bologna
(74) *Attorney, Agent, or Firm* — Barnes & Thornburg LLP

(57) ABSTRACT

Methods and devices are disclosed for acquiring depth resolved aberration information using principles of low coherence interferometry and perform coherence gated wavefront sensing (CG-WFS). The wavefront aberrations is collected using spectral domain low coherence interferometry (SD-LCI) or time domain low coherence interferometry (TD-LCI) principles. When using SD-LCI, chromatic aberrations can also be evaluated. Methods and devices are disclosed in using a wavefront corrector to compensate for the aberration information provided by CG-WFS, in a combined imaging system, that can use one or more channels from the class of (i) optical coherence tomography (OCT), (ii) scanning laser ophthalmoscopy, (iii) microscopy, such as confocal or phase microscopy, (iv) multiphoton microscopy, such as harmonic generation and multiphoton absorption. For some implementations, simultaneous and dynamic aberration measurements/correction with the imaging process is achieved. The methods and devices disclosed can provide wavefront sensing in the presence of stray reflections from optical interfaces.

21 Claims, 13 Drawing Sheets

METHOD FOR DEPTH RESOLVED WAVEFRONT SENSING, DEPTH RESOLVED WAVEFRONT SENSORS AND METHOD AND APPARATUS FOR OPTICAL IMAGING

FIELD OF THE INVENTION

The present invention relates to a method of wavefront sensing and to wavefront sensors with enhanced performance and to a method using the same in an optical mapping apparatus which can be used to supply high resolution images from essentially transparent objects or tissue via aberrated paths.

Methods and devices are presented for enhancing the performance of wavefront sensors using principles of low coherence interferometry (LCI). These wavefront sensors can operate under large stray reflections in the optics and therefore lead to simplification of adaptive optics (AO) assisted imaging instruments and to improvement of their performance. Solutions are presented for optical imaging configurations employing such sensors to control a wavefront corrector in accordance with the aberration information collected by the sensor in order to obtain optical coherence tomography (OCT) images, confocal microscopy (CM) images, phase microscopy (PM) or nonlinear optics microscopy images, such as in two or three photon absorption, second and third harmonic generation which involve multiphoton microscopy (MM), all with less aberrations. In particular, but not exclusively, the invention relates to the imaging of the retina in-vivo, in which case enhanced quality OCT and scanning laser ophthalmoscopy (SLO) images are generated.

BACKGROUND OF THE INVENTION

Different methods of wavefront sensing are known, psycho-physical, involving the human subject and objectives, such as refractive, laser ray tracing (LRT), Shack-Hartmann (SH) wavefront sensors (WFS), pyramid (P) wavefront sensors.

So far, all these methods provide 2D aberration information. Each method and associated device sample the transversal distribution of aberrations. LRT, by collecting a limited number of points in transversal section of the beam while moving the investigating beam parallel to itself before incidence on the cornea. To enhance the speed, an advanced LRT method is presented in U.S. Pat. No. 6,561,648 to D. Thomas, where more than one beam at a time is produced by a spatial light modulator (SLM) and used to provide a LRT type wavefront sampling. However, the method cannot provide depth resolved wavefront information due to the low numerical aperture associated to each beamlet created by the SLM.

Principles of SH/WFS are described in several prior publications, such as J. J. Widiker, S. R. Harris, and B. D. Duncan, "High-speed Shack-Hartmann wavefront sensor design with commercial off-the-shelf optics," Appl. Opt. 45, 383-395 (2006) and A. Chernyshov, U. Sten, F. Riehle, J. Helmcke, and J. Pfund, "Calibration of a Shack-Hartmann sensor for absolute measurements of wavefronts," Appl. Opt. 44, 6419-6425 (2005). A SH/WFS uses a limited number of lenses in a lenslet array and the beams traversing such micro-lenses have small diameters. A pyramid sensor uses a limited number of pixels according to the number of pixels in 2D array cameras. Again, due to the limited numerical aperture in each of the beams associated with microlenses or photodetectors, SH/WFS or P/WFS, the WFS has little sensitivity to depth in the object. The lenses in the SH/WFS sample a tiny part of the interrogated beam, for 10×10 number of lenses, less than 1/10th of the beam is intercepted by the micro-lens. Given their focal length, usually 1 mm-1 cm and their diameter, 0.5-5 mm, the confocal depth range of each measuring channel is hundreds of microns or millimeters. Each lens in the lenslet operates like a confocal microscope (CM) channel. Therefore, the deviation of the focused spot from the node of the grid corresponding to a non-aberrated beam for that lens represents an integration of aberrations over the depth range of the corresponding CM channel in the SH/WFS. This makes the SH/WFS insensitive to depth variations of aberrations, or more precisely, the spots are deviated from the ideal wavefront grid by quantities which represent averages of aberrations over the depth of focus of the confocal microscopy channel of each lens in the lenslet array. This depth of focus is comparable with the 1 mm tissue thickness of interest or much larger.

Systems are also known which combine WFSs with imaging configurations, such as those disclosed in U.S. Pat. No. 5,949,521, WO2003/105678 A2. All the WFSs presented and the systems using them have the disadvantage that for thick objects, the variation of aberration with depth is disregarded. The aberration introduced depends on the depth where the reflection originates from and such information is not acquired. Acquisition of depth resolved aberration is especially important in microscopy, where shallow layers deteriorate the curvature of the beam.

A general problem with prior art configurations is that they acquire aberration information from a large depth range of the object investigated. Their depth range is that determined by the focus elements and apertures within the sensor. For instance, when the sensor is a SH/WFS, each lens in the lenslet array together with all other parts in the optics interface between the lens and the object implements a CM channel with a very large depth of focus, sometimes larger than the tissue or the microscopy specimen examined.

As another problem of prior art, the depth resolved variation of aberration is ignored due to the principle of imaging involved. The paper "Adaptive optics parallel spectral domain optical coherence tomography for imaging the living retina" by Yan Zhang, Jungtae Rha, Ravi S. Jonnal, and Donald T. Miller, published in Opt. Express, Vol. 13, No. 12, pages 4792-4811 presents a combination of a SH-WFS controlling a deformable mirror, with a spectral domain OCT (SD-OCT) camera based on a free-space parallel illumination architecture. A B-scan (cross-section) of the retina is obtained, but for points along A-scans in the image, there is no alteration of the correction to take into account the aberration variation with depth. No such information is acquired, while it is expected that the aberrations vary as the coherence gate of the OCT channel progresses in depth. On the other hand, even if depth resolved aberration information was provided, the OCT method employed cannot be used in generating a corrected OCT image depending on the variation of aberrations with depth, as the SD-OCT is based on collecting A-scans under a fixed focus.

Due to the reasons mentioned above, an average correction is achieved only, based on the average of aberrations over the depth of range of the wavefront sensor.

There are also microscope specimens where the shallow layers distort the imaging of deeper layers.

As another disadvantage of prior art is that WFSs use sensitive photodetectors or arrays of photodetectors which are easily disturbed by stray reflections in the optics. For instance, reflections form lenses in the interface optics of microscopes and reflections from cornea affect the operation of the WFSs. These have to be eliminated in microscopes and in the OCT and SLO systems for imaging the eye. Therefore, spatial filters are used, which are not 100% functional, i.e. they do not eliminate the reflections from the different interfaces or from the cornea totally. Therefore, the cornea is placed off-axis, which introduces aberrations. This is achieved by working off-axis with one of the beams, either that of the WFS reference beam or the imaging beam, as disclosed in the U.S. Pat. No. 6,264,328 (Wavefront sensor with off-axis illumination). In this case, the beam used for the WFS cannot be shared by the imaging instrument, because the imaging beam has to cross the middle of the pupil at different angles.

The problem of stray reflections determines the use of single path correction configurations, where a thin beam is sent to the eye and aberrations are picked up by the emerging beam coming out of the eye. In this case, the correction cannot be applied dynamically, as described in the paper Adaptive-optics ultrahigh-resolution optical coherence tomography, by B. Hermann, et al, published in Optics Letters, Vol. 28, No. 18, 2004, 2142-2144. This article presents a flying spot system OCT, single path correction and sequential work of OCT and AO channels.

In double path, the same beam towards the object is shared by the WFS and the imaging instrument, in which case the on-axis corneal reflection saturates the CCD camera in the WFS as mentioned above.

Also, in double path correcting configurations of fundus cameras, SLOs or OCTs which use lenses between the scanners and the eye, the stray reflections from the lenses affect the WFSs. Therefore, curved mirrors are preferred to lenses with the disadvantage of increased set-up size and cost.

Therefore, better WFSs are needed, which can provide aberration information at each depth in the sample, either a thick specimen in microscopy or the retina.

WFSs are also needed, less sensitive to stray reflections in the optical configuration.

In addition, chromatic aberrations are often ignored. Previous WFS studies have used a series of filters to select the wavelength measurements and have performed the wavefront measurements one after another, as described in the article "Axial chromatic aberration of the human eye," published by R. E. Bedford and G. Wyszecki in the Journal of the Optical Society of America 47, 564-565 (1957).

The system described in the article "Ocular aberrations as a function of wavelength in the near infrared measured with a femtosecond laser," published by E. Fernandez, A. Unterhuber, P. Prieto, B. Hermann, W. Drexler, and P. Artal in Optics Express 13, 400-409 (2005) was used to show that defocus in the eye can change by up to 0.4 diopters in the human eye when the wavelength is changed within a 200 nm range in the IR range centered on 800 nm.

The evaluation of chromatic aberration is therefore essential for achieving good performance in high resolution imaging of the retina.

The article "Coherence-gated wave-front sensing in strongly scattering samples", Marcus Feierabend, Markus Rückel, and Winfried Denk, published in Optics Letters, (2004) Vol. 29, No. 19, p. 2255-2254 and the US application 2006/0033933 disclose a method based on low coherence interferometry to produce 3D distribution of the scattered wave by analyzing its phase. The coherence gated (CG) information is then followed by sampling the 3D data into spatial arrays corresponding to SH apertures. Such apertures are virtual. The time to work out the interference signal is relatively high and such a procedure is subject to cross talk between pixels, which alters the phase information. These deficiencies restricted the development of the method. A lenslet array is also suggested instead of the virtual evaluation of electrical fields on sub-arrays, but this is placed in the object arm. This prevents using the same beam sent to the object for imaging. Imaging and wavefront sensing at the same time or with the same beam is not possible. In both cases, using a virtual lenslet or a real lenslet array, the method relies on phase calculations. The move from interferometric to Shack-Hartmann sensing was motivated by the need to avoid phase unwrapping and phase stability problems of the interfering sensors. The article and patent by Markus Rückel, and Winfried Denk mentioned above require phase unwrapping for large aberrations.

A major problem with the prior wavefront sensing technology, with or without coherence gating, is that the information is acquired and provided en-face. Progress in fast OCT imaging requires such information and potential correction to be provided in cross-sections and not in en-face orientation.

Thus, a need exists for addressing the problems of the prior art mentioned above using novel principles of WFS. Novel optical configurations are also needed which can employ such enhanced WFS in improving the imaging resolution.

SUMMARY OF THE INVENTION

The present invention solves the above problems by means of methods, devices and configurations of depth resolved wavefront sensors and apparatuses employing them. Progress in the combination of OCT and AO requires that the aberration correction is that corresponding to the layer being imaged. The present disclosure describes wavefront sensors where LCI is used to narrow their depth resolution. This leads to WFSs that can provide 3D information on aberrations and not 2D only, like the information provided by the prior art WFSs.

The invention discloses devices and methods which can provide depth resolved aberration information, or at least are less sensitive to stray reflections coming from other depths than those inside the object. WFSs less sensitive to reflections from lenses are needed, with the advantage that lenses could be used in the interface optics, which make all optics layout more compact. In the same spirit, if the WFS is less sensitive to cornea reflections, then perfect on-axis imaging becomes feasible, advantageous for aberrations-free imaging systems. The invention provides improved results, less sensitive to the chromatic aberration.

Thus, in a first aspect of the present invention, there are provided different configurations of depth resolved WFSs.

In this respect, a first embodiment presents a laser ray tracing coherence gated wavefront sensors (LRT/CG-WFS). Two versions are presented, (i) operating under low coherence excitation and (ii) using a swept source and operating based on principles of swept source OCT. In this case, dynamic spectral compensation of focus change can be achieved.

In a second embodiment, the invention describes a Shack-Hartman coherence gated WFS (SH/CG-WFS). Two versions are presented: (i) using a swept source and operating based on principles of swept source OCT and (ii) operating under low coherence excitation. When using a swept source, dynamic spectral compensation of focus change can be achieved as well.

In a third embodiment, a pyramid sensor is provided. This can also operate under low coherent or swept source excitation.

In a second aspect, improved attenuation of the stray reflections is achieved by using balance detection, where two photodetectors, two smart chips or two CMOS or CCD arrays are used, whose signals are deducted to double the strength of the interference signal and cancel the common mode signals.

In all these embodiments, depth resolved aberrations are obtained by superposing a reference beam over the object beam returned from the object. The reference beam is derived from the same source as that providing illumination of the object to produce the aberration mapping. If the source used has low coherence, then interference is produced only when the optical path difference (OPD) between the object beam and the reference beam is less than the coherence length of the source. The coherence gating principle is achieved either by using a broadband source and TD-OCT or a swept source and SS-OCT. The coherence gating may be used to provide depth resolved aberration information from the sample object, or it may be used for the reduced scope of eliminating stray reflections from the interface optics.

By using polarisation sensitive components, such as phase plates and beamsplitters, the information collected by the two cameras, 33 and 33', can be used to provide polarisation depth resolved aberrations.

In a third aspect of the invention, there is provided an optical mapping apparatus comprising: (i) one or two of the imaging channels, which could be any of or combination of an optical coherence tomography (OCT) channel, a confocal imaging channel, a multiphoton microscopy channel, and (ii) an adaptive optics (AO) system including: a wavefront corrector and a wavefront sensor, where the depth where the wavefront sensor collects aberrations from is correlated or coincide with at least one of the:
  (i) focus of the OCT imaging channel;
  (ii) depth position of the coherence gate of the OCT imaging channel;
  (iii) focus of the confocal imaging channel;
  (iv) nonlinear optics gate created by nonlinear optics effects in samples by focusing high power short pulse-width lasers in multiphoton microscopy (MM).

In this way, the depth wherefrom an image is collected in the OCT imaging channel or in a SLO, or in a CM channel, or in a MM channel, in one or more such channels, is selected in synchronism or is substantially the same with the depth where the WFS collects the aberrations information from. The U.S. Pat. No. 7,466,423 (Podoleanu) describes a combined en-face OCT/SLO under AO correction. The disclosure has the disadvantage that the WFS has a wide depth of focus and suffers from reflections in the interface optics.

In a fourth aspect, the invention provides for a protocol of measuring and imaging steps, where depending on the LCI regime used by each sub-system, CG-WFS and imaging subsystem, different possibilities exist for inter-twining the aberration collection step with the imaging step.

In a fifth aspect, the invention provides a CG-WFS for microscopy, equipped with dynamic focus. Such embodiments can sequentially operate in WFS or imaging mode, based on full field OCT technology on either regime. The same procedure and devices for dynamic focus can be included into a separate OCT imaging channel working in parallel with the CG-WFS.

In yet another aspect, the invention provides for a sequential operation of the WFS in two possible regimes: (i) as a standard sensor, by blocking the reference path towards the 2D arrays and (ii) as a coherence gated WFS. In this way, information on the aberrations in the path from the object is acquired in the (i) regime and information from the aberrations in the double path, towards and from the object is acquired in the (ii) regime. Such information can be combined to provide the aberrations in the path towards the sample, essential for performing nonlinear microscopy, where focusing better the excitation light is more important than the resolution in collecting the backscattered signal.

BRIEF DESCRIPTION OF THE DRAWINGS

Other features of the present invention, as well as other objects and advantages attendant thereto, are set forth in the following description and the accompanying drawings in which like reference numerals depict like elements. Accordingly, various embodiments of the optical imaging apparatus of the present invention will now be described by reference to the following drawings wherein.

Figure 1:
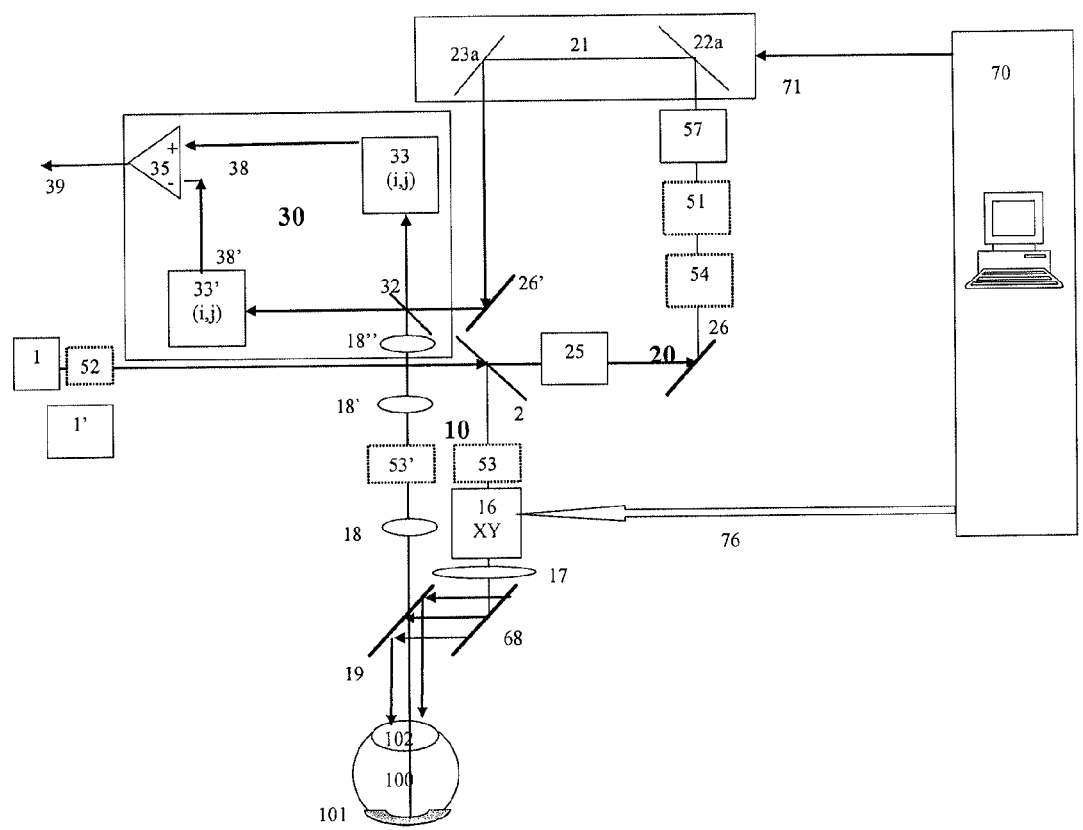
FIG. 1 shows a first embodiment of the present invention where a depth resolved LRT wavefront sensor is presented.
Figure 3:
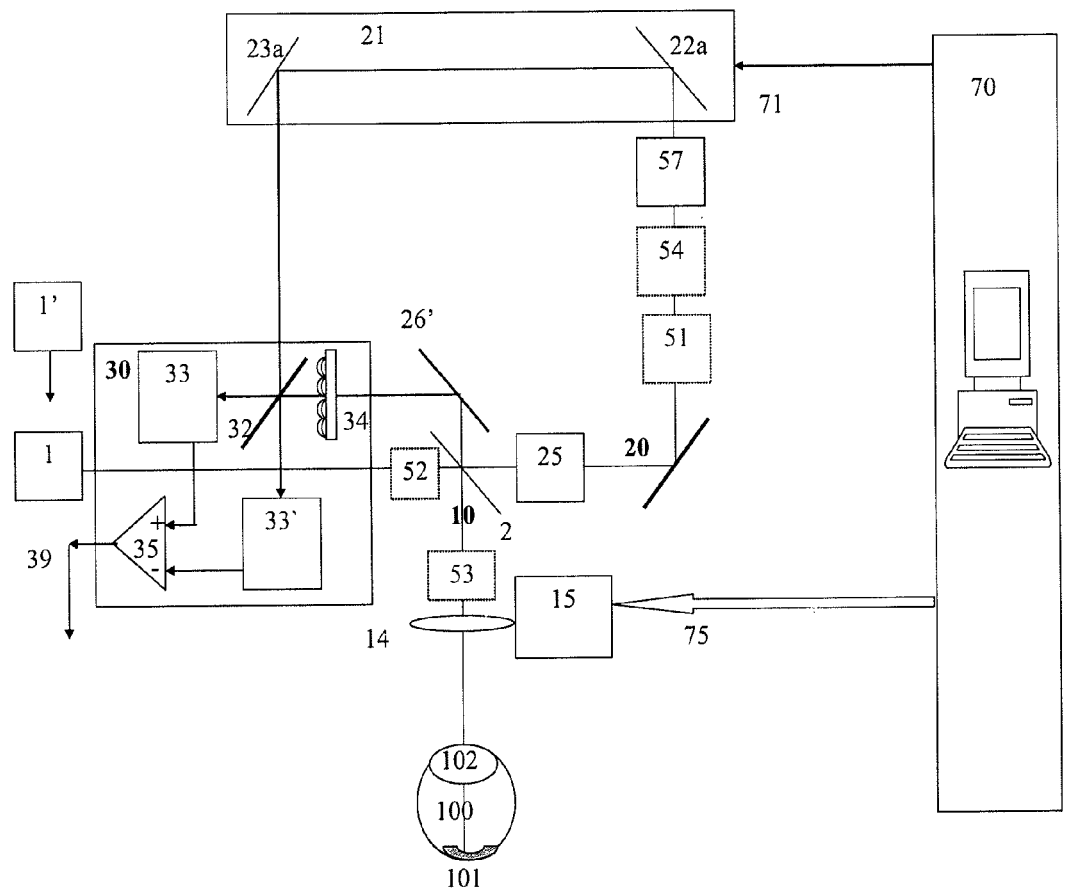
FIG. 3 shows a second embodiment of the present invention where a depth resolved Shack-Hartmann wavefront sensor is presented.
Figure 8:
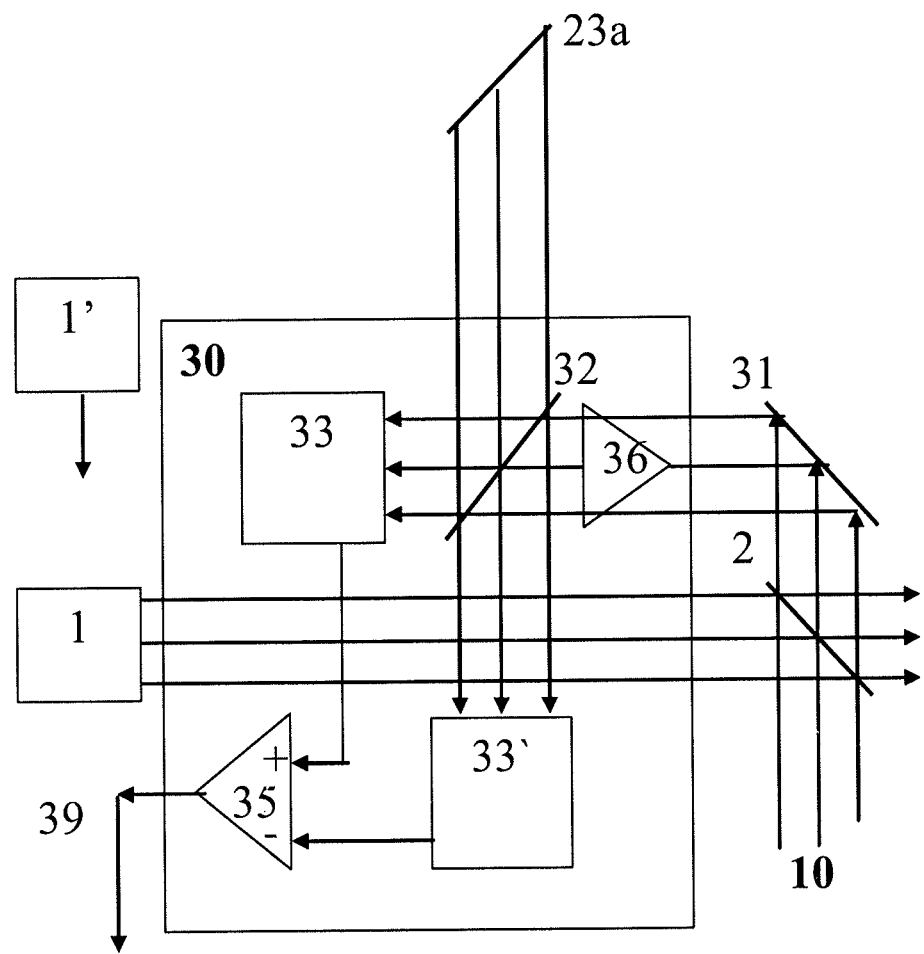
FIG. 8 shows a third embodiment of the present invention where a depth resolved pyramid wavefront sensor is presented.

The embodiments in FIGS. 1, 3 and 8 can operate under broadband source excitation, operating according to TD-OCT principle or can operate using a swept source and implement the principle of SS-OCT.

Figure 9:
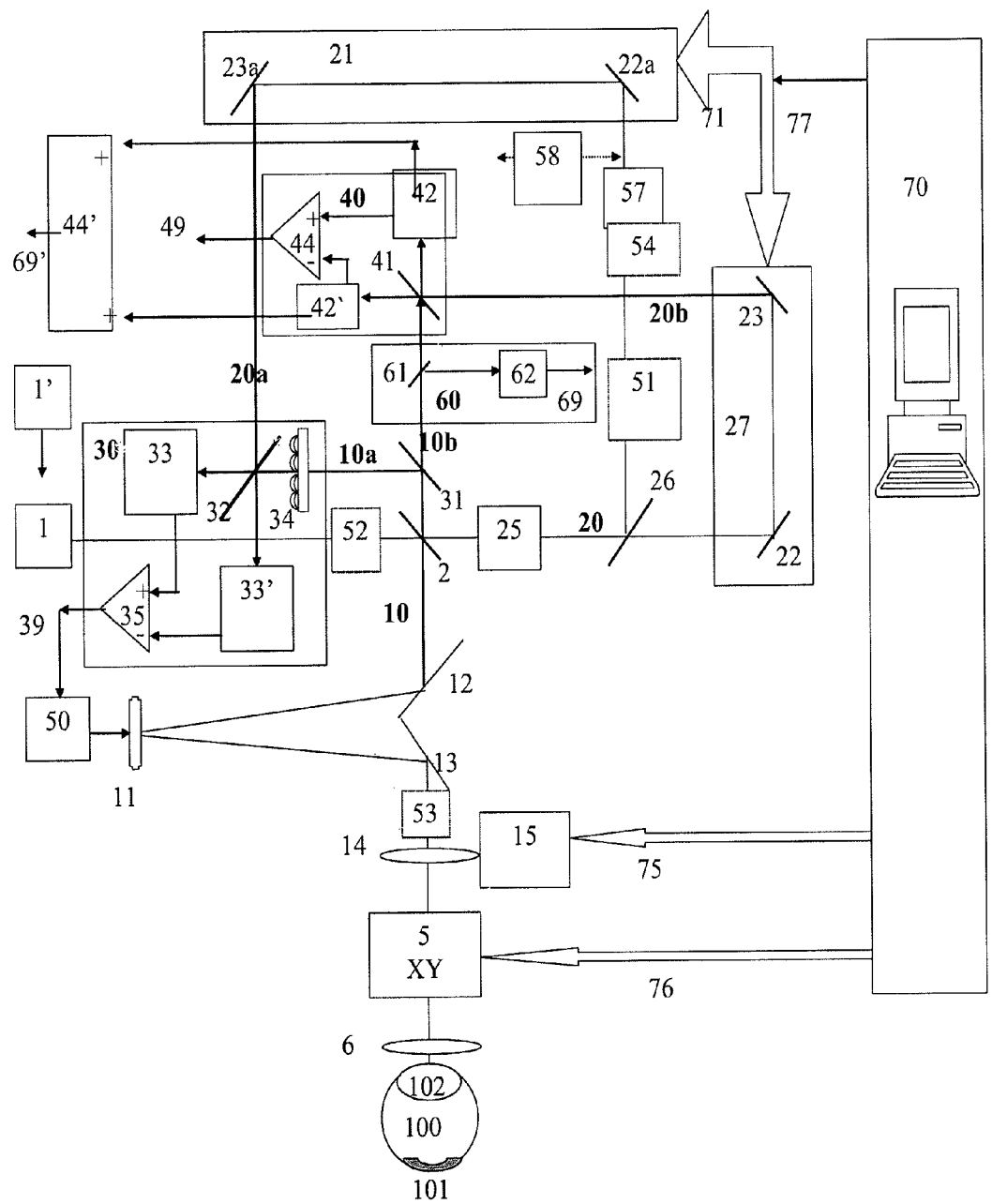

FIG. 9 shows an embodiment of the present invention where a SH/CG-WFS is combined with an imaging instrument.

Figure 10:
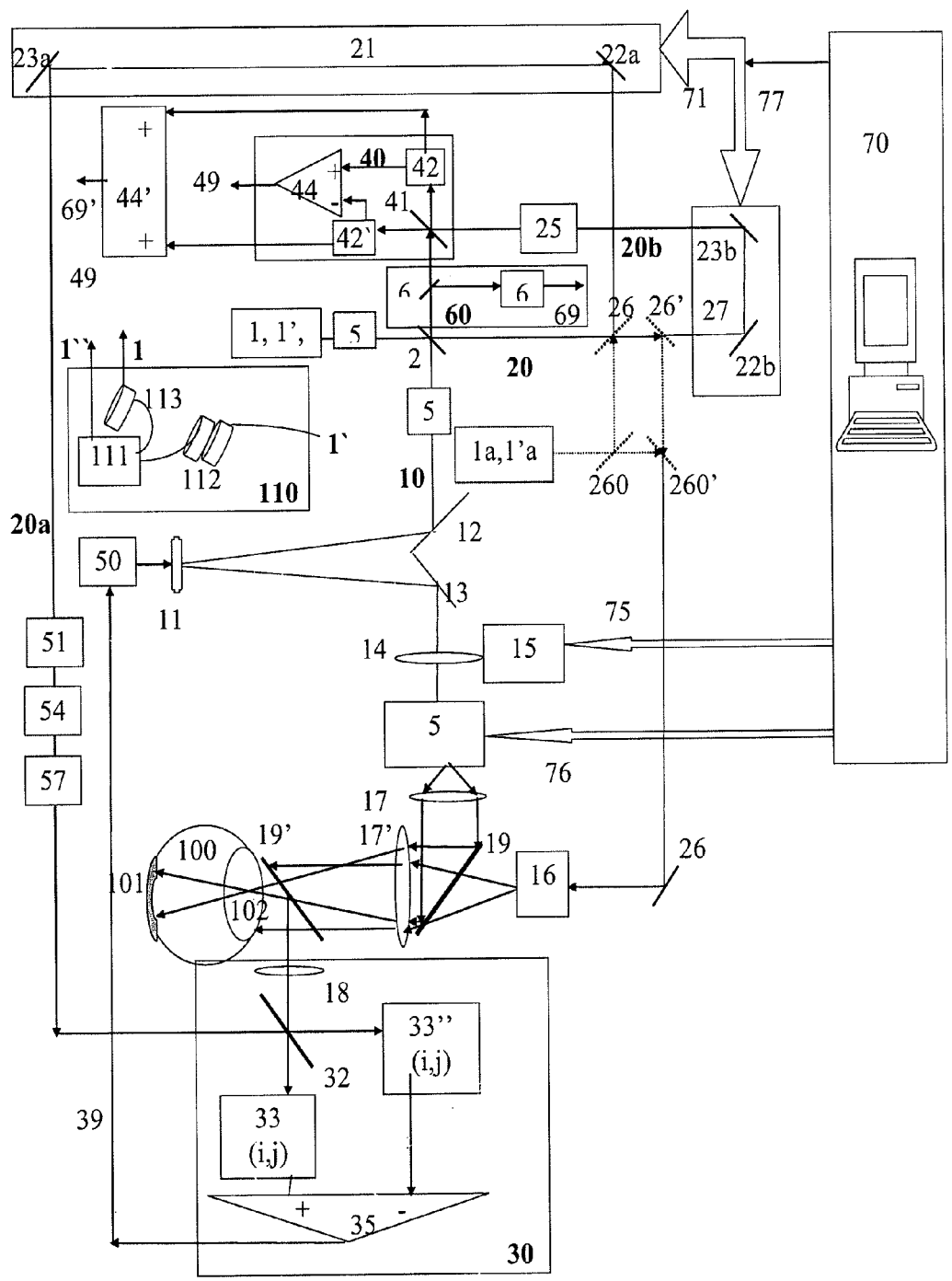

FIG. 10 shows an embodiment of the present invention where an LRT/CG-WFS is combined with an imaging instrument.

Figure 11:
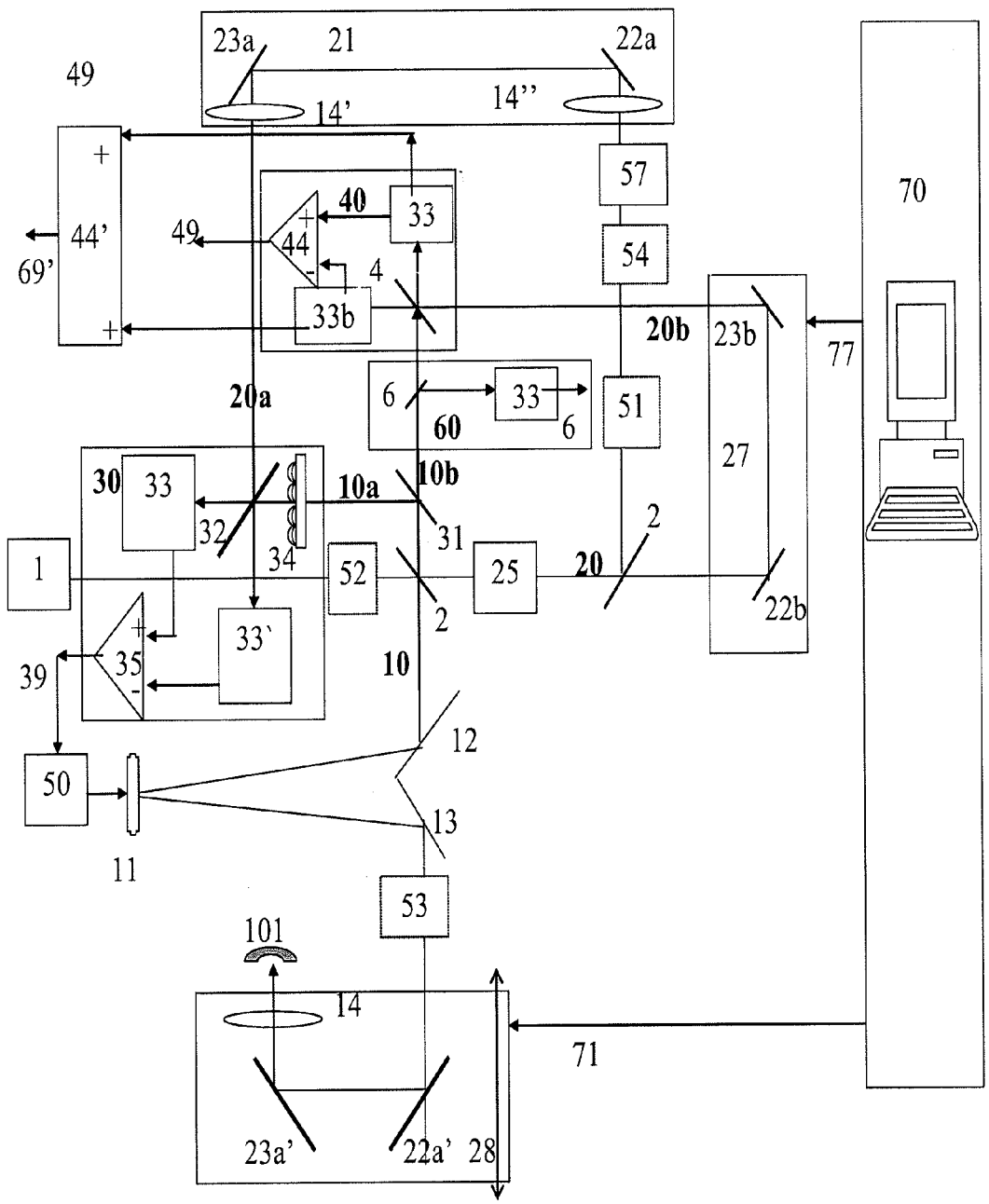

FIG. 11 discloses an embodiment where the foci of the lenslet array are held in coherence when scanning the depth in the sample.

DETAILED DESCRIPTION OF THE PREFERRED EMBODIMENTS

LRT/CG-WFS

FIG. 1 discloses a first embodiment of the present invention. A low coherence interferometry principle is incorporated into a first embodiment of a WFS, operating according to the LRT method.

Light from a low coherent optical source, 1, is split by a splitter 2 towards a XY scanning means 16, which transversally scans the output beam via an interface optics 17, a mirror 68, and a splitter 19, over the cornea aperture, 102, of the eye 100, to focus on the retina 101. The blocks 16 and 17 are shown separately, however they could be interleaved, like the line scanner, a galvo-mirror, a piezo, an acousto-optic deflector, etc, followed by lenses or curved mirrors, and then by a frame scanner consisting of one of the possible means of scanning known. The scanning means 16 and interface 17 could also be implemented using a spatial light modulator (SLM), such as an addressable liquid crystal digital spatial modulator or other means known in the art. Light returns from the retina, 101, and via splitter 32 is incident on different pixels of the photodetector array 33, usually a CCD or a CMOS array, part of the wavefront sensing processing block 30. If the eye is ideal, then the beam returns to the center of the array 33. In case the beam is not refocused by a lens to the focal point on axis, then the beam will go to different pixels of the CCD array. Aberrations deviate the backscattered beam away from the reference position. Due to aberrations, the beam moves laterally across the photodetector array 33, to pixels (n,m). Using 16, several points within the cornea 102 are sampled. For each transversal point within the eye input aperture, the position of the returned spot, (n,m) is registered as a pixel in the photodetector array. A telescope using focusing elements 18, 18' transfers the aerial cornea image to the final lens, 18" which focuses the beam emerging from the eye onto the array 33.

Up to here, the description is that of a prior art LRT device, where the aberration information in the form of deviation of beam from a reference point represents an average of aberrations for a large depth of focus, as determined by the confocal equivalent aperture of the imaging system. This could be as large as 0.5 mm to several mm when the object is the retina. According to the invention, a method and configuration are provided to restrict the depth interval of the aberration information so collected, and register the position (n,m) versus axial depth, z within the object. To this end, a reference beam is superposed on the array 33. A reference beam is split from the incident beam by the optical splitter 2, along path 20. Via an optional mirror 26, the reference beam is sent to mirrors 22a and 23a, mounted on the translation stage 21, towards optional mirror 26', and then towards splitter 32. To select the depth position where signal originates from within the object, the coherence gate principle is employed and the depth range is explored by moving the stage 21, which changes the optical path difference between the object optical path 10 and the reference path 20. To attenuate the reference path, an optional neutral density filter, 51 is used. The object path 10 starts at splitter 2, goes via 16, 18, splitter 19 to the eye 100, from the retina 101 returns back via splitter 19, towards splitter 32. The reference path 20 starts at splitter 2, goes via mirrors 26, 22a and 23a, mirror 26' to splitter 32. To compensate for dispersion in the object arm, a BK7 block, 57, or a combination of glass materials used in the object arm with a matched length are employed.

A PC 70 controls the sequence of transversal position selection, by actuating on the XY scanner 16 via line 76 with the selection of different depth positions, by moving the stage 21, under control line 71.

For further refinement of the method, another camera, 33' is used in the wavefront sensing processing block 30 to eliminate the stray reflections in a balance detection configuration. The signals from the two cameras 33 and 33' are deducted in the differential amplifier 35 to provide the wavefront information along output line 39. Based on a principle known in the art of OCT, the interference signal is up into one camera, 33, and down in the other, 33', due to a $\pi$ phase difference between the signals reflected and transmitted through splitter 32. By deducting the two output signals, the interference signal strength is doubled and the bias, containing stray reflections and dc terms, is largely attenuated.

As an improved operation, several other configurations known in the art are feasible by using waveplates and manipulation of the polarisation of the source light and of the polarisation of light coming from the target. If the source, 1, is not polarised, then a polariser, 52, is used to produce linear polarised light. Then, a quarter wave plate is placed in the object path, 53, and a similar wave plate, 53', oriented at 45 degrees from the incident plane of the linear polarisation. In this way, circular polarised light is sent to the target. If the target is a mirror, then the reflected light will have opposite helicity and after 53' will exhibit linear polarisation, with vibration orientation perpendicular to the incident direction prepared by 52. In the reference path, light traverses a half-wave plate, 54, that is used to rotate the polarisation by 45 degrees. The beamsplitter 32 is in this case, polarisation sensitive. This separates two orthogonal states from natural light. In this way, the two cameras generate signals that are out of phase by $\pi/2$. The principle is known in the art of interferometry, as described in "Interferometric ellipsometry", by H. F. Hazebroek, A. A. Holscher, published in *J. Phys. E: Sci. Instrum.* 6, 822-826, (1973) and in "Polarization-sensitive low-coherence reflectometer for birefringence characterization and ranging", by M. R. Hee et al, published in *J. Opt. Soc. Am. B*, (1992), 9, No. 6, 903-908.

In this case, instead of using the cameras to provide signals with a $\pi$ phase difference between them and subtract them, the images of the two cameras, H and V are used to provide several facets of polarisation information: a polarisation insensitive measurement, I (given by the sum of squares of the two arrays, pixel by pixel, $R(x,y,z) \propto H^2+V^2$), birefringence, B (by evaluating the arc-tangent of the ratio of the two camera signals, pixel by pixel, $$\delta(x, y, z) = \tan^{-1}\left(\frac{V}{H}\right)$$

and the rotation of the birefringence axis, $\theta$, (according to equations given in the two publications above). The three quantities I, B, $\theta$ for instance, could be used to quantify depth resolved aberrations along two orthogonal polarisation axes in the sample. This could be used when investigating samples that manifest birefringence, to provide depth resolved aberrations that are also dependent on the polarisation of the incoming light. Even if depth resolved aberrations are not to be evaluated, such a set-up can produce enhanced signals from birefringent materials.

The elements 52, 53, 53' and 54 are in dashed line to show that they are optional.

5.1. Time-Domain Low Coherence Interferometry (TD-LCI) Based WFS

Phase shifting interferometry is applied using a phase modulator 25. This can implement subwavelength changes of OPD in steps of $\lambda/m$, with a typical value for m=3. For m=3, the signal at each pixel of the array 33 (33') is obtained from three values, $I_1$, $I_2$ and $I_3$ of the same pixel obtained for the 3 steps by:

$$s = \sqrt{(I_1-I_2)^2+(I_1-I_3)^2+(I_2-I_3)^2} \quad (1)$$

If m=3, then for a central wavelength of $\lambda$=750 nm of the source 1, the small steps are 250 nm/2 each. The phase modulator 25 can use an electro-optic or magneto-optic modulator. Simpler, a piezo driver can be used to move mirrors 22a or/and 23a. Alternatively, for each position of the scanning beam deflected by the XY scanner 16, the translation stage 21 can be moved continuously and frames are collected by the array 33 (and 33') continuously. For each successive m frames, the fringe visibility is calculated and this leads to the value of the (m,n) pixel. Alternatively, the phase modulator 25 is used to produce at least m=3 phase shifts.

This method delivers an en-face full field (FF) type of OCT image. Within this image, N×N spots are found using a centroiding algorithm.

If balance detection is used with two cameras, then the $I_i$ in equation (1) above represent the signal delivered by the differential amplifier 35.

TD-LCI requires a broadband source, 1. However, as disclosed below, this method may also be used in conjunction with a swept optical source, 1', where the arrays 33 and 33' deliver images at time intervals equal or larger than the time to tune the swept source within its tuning bandwidth. In this case an integration of the time domain interferometer is performed over all wavelengths within the tuning bandwidth that needs to have sufficient width to ensure the necessary depth resolution.

5.2. Swept Source OCT Based WFS

In comparison with the FF-OCT concept used above, the SS-OCT concept provides more signal to noise ratio and allows increased speed. The only problem is to organise the data in the form of an en-face image. This can be achieved using the embodiment in FIG. 1. The source 1 is replaced with a tunable (swept) laser, 1'. In order to achieve the same depth resolution as using the large bandwidth source 1, the swept source 1' is tuned within the same bandwidth, $\Delta\lambda$, as that delivered by the low coherent source 1. Spectral OCT using a swept source is a longitudinal OCT method as described in the article: "Three-dimensional and C-mode OCT imaging with a compact, frequency swept laser source at 1300 nm, by R. Huber, M. Wojtkowski and J. G. Fujimoto, J. Y. Jiang and A. E. Cable, published in Optics Express, Vol. 13, No. 26, (2005), pp. 10523-10538.

The depth scanning is performed fast by tuning the frequency of the laser, 1'. Such tuning can take place at much faster rates than achievable in TD-OCT which makes such sensors suitable for fast acquisition of depth resolved wavefront information. Although the frequency scanning could achieve over 100 kHz range, the WFS cannot achieve fast rates of reading due to the limited frame rate of operation of the CCD camera 33 (and 33').

On the other hand, using a tunable laser source, there is no need for phase shifting interferometry, so in this case, there is no need for a phase modulator 25. (However, a phase modulator or a frequency shifter could still be used to double the range of SD-OCT as described in the article: "Heterodyne Fourier domain optical coherence tomography for full range probing with high axial resolution", by Adrian H. Bachmann, Rainer A. Leitgeb, Theo Lasser, published in Opt. Express, Vol. 14, No. 4, (2006), pp. 1487-15. In this case, the modulator 25 operates as a frequency shifter and another frequency shifter modulator is placed in the object arm (not shown), or two such modulators are placed in the same arm, object and reference, driven at suitable RF frequencies whose beat creates a frequency carrier for the SD-OCT information. By synchronizing the frequency scanning of source 1' with the photodetector reading in 4 sequences, within one beating period, the complex Fourier transformation is evaluated. This allows elimination of the mirror terms and doubling the OPD range.

In addition, when applying the swept source principle, correction for the chromatic aberration in the interface optics or in the sample can be implemented in synchronism. For instance, it is known that for a 200 nm bandwidth, a defocus error of 0.4 diopters is typical when imaging the retina in the human eye, as shown in the article published by E. Fernández in Optics Express mentioned above.

Let us say that the array 33 (33') uses N×N pixels. The 3D wavefront information can be obtained in the following steps:

1. According to principles known in swept source OCT and low coherence interferometry, for each pixel (n,m) where n=1 to N and m=1 to N, an A-scan is inferred by tuning the laser 1' within the bandwidth $\Delta\lambda$ and Fourier transforming the signal generated during such tuning. If the source is tuned within an interval $\Delta\lambda$ and M frames (for M different optical frequencies) are acquired, then Fourier transformation (FFT) of the M points of the photodetected signal delivers an A-scan in a depth range of approx.: $0.25M\lambda^2/(\Delta\lambda)$ with a depth resolution of approx.: $\lambda^2/\Delta\lambda$. If the M points collected are not for equidistant values of optical frequency, then a linearization and interpolation procedure, according to means known in the art is used before the FFT.

2. Using the N×N A-scans such collected, a 3D volume, $V_a$ is generated.

3. Then, out of the volume $V_a$, a number of en-face frames are inferred, each containing corresponding deviated spots, which determines the aberration information for that given depth value of the en-face frame within the $V_a$ volume of the object.

4. In each such frame, deviations of the spots from the on-axis location (or reference position, depending on the LRT implementation) are evaluated.

5.2.1. 3D Depth Resolved Aberrations

To achieve the same performance as that of a commercial WFS based on the SH principle, the LRT/CG-WFS should perform the same level of sampling of the wavefront. A commercial SH/WFS such as HASO, produced by Imaging Eye, Paris, uses 32×32 lenslets and for each spot, 16×16 pixels are allocated on the CCD camera. This functionality is achieved with a CCD camera of 512×512 pixels (32×16=512), read at a frame rate of 50 Hz. To reproduce the same results as the HASO, the LRT method should be repeated for i×j different values of sampling the cornea, i.e. for 32×32 times for different positions, (i,j) of the incident beam on the cornea, addressed by the galvoscanner 16.

There are fast cameras that can be used to acquire n×m=16×16 pixels at frame rates of F=1 kHz or higher. An equivalent coherence length $l_c$=10 μm which determines a depth resolution of $l_c/2$ requires a tuning range of $\Delta\lambda$~26 nm at 800 nm central wavelength. To achieve OPD=1 mm depth range, the number M of spectral samples should be double the numbers of peaks in the channeled spectrum, which, for an $OPD/l_c$=100, should be 200. At a 1 kHz frame rate, this is achieved in a time M/F=0.2 s. The tuning rate required for the source 1' is to perform a change of $\delta\lambda$~26/200=0.13 nm change in 1 ms which can be mechanically achieved, i.e. 26 nm in T=0.2 s. If faster cameras are used, then a faster tuning rate laser 1' is required. This is not a problem, as rates of over 100 kHz are now achievable, as described in the articles: "Fourier Domain Mode Locking (FDML): A new laser operating regime and applications for optical coherence tomography, by R. Huber et al, published in Optics Express, (2006), Vol. 14, No. 8, pp. 3225-3237 and in "Ultra-high-speed optical coherence tomography with a stretched pulse supercontinuum source," by S. Moon and D. Y. Kim, published in Opt. Express, (2006), Vol. 14, pp. 11575-11584.

By the end of the acquisition, M=200 sampling points are collected for each pixel in the 16×16 array. Next, if the points collected are not for equidistant values of optical frequency (or wavenumber), then a linearization and interpolation procedure, according to means known in the art is used before a FFT is evaluated to generate an A-scan for each (n,m) pixel. These 16×16 reflectivity profiles are then used to assemble a 3D cube of OCT data. Next, p=200 en-face planes can be sliced in the cube, at every 5 microns axial distance, $z_p$ to represent the position of spots corresponding to lateral deviations in the plane of the 16×16 pixels versus axial depth, $z_p$. In each such depth plane, defined by $z_p$, a centroiding algorithm finds the $(n_p,m_p)$ center of the spot, and hence the slope associated to its position, $h_p$. Let us suppose that the FFT is performed at high speed, state of the art digital processing can perform FFT of 1024 points of 14 bits in 1 microsecond. For our example, 200 samples would require 200 ns, which for 16×16 samples raises the time to 50 ms. Time is also required for 3D synthesis and the centroiding, for which, we could estimate that in total with the FFT it can be performed in $T_{FFT+3D1+C}=0.1$ s. This means $T+T_{FFT+3D+C}=0.3$ s. Then, 32×32 repetitions are required, for each (i,j) position of the beam over the cornea aperture using the scanner 16. This raises the time to $32\times32\times(T+T_{FFT+3D+C})=307$ s.

Possibly, the repetitions of data collection may proceed immediately after acquiring one tuning scan, which at 1 kHz frame rate is 0.2 s, memorize all 16×16 pixels frames and repeat 32×32 times, in which case only 204 s are needed, with FFT, 3D constructions, en-face slicing and centroiding performed by the end for all 16×16×32×32=262144 spectrally sampled axial profiles, each of 200 points.

This procedure is feasible for microscopy, however for the eye the time is too long and a faster procedure is described below.

5.2.2. A Single En-Face Plane of Aberrations Placed at a Shallow Depth

Let us say that we are not interested in providing depth resolved aberration from the whole volume of the tissue, but data similar to a standard LRT method, free of stray reflections only. In this case, the number of frames acquired could be reduced by a factor of 10, to M=20. Using 20 frames, only 10 peaks can be sampled in the channeled spectrum, this means an OPD~$10 1_c$=100 microns, i.e from a 50 μm depth. In this case, the acquisition time could be reduced by a factor of 10 to T=20 ms only. The time for 3D and centroiding remains the same, while the time for FFT becomes at least 10 times smaller, 5 ms, which with the values above leads to $T_{3D+C+FFT}=50+5=55$ ms, determining $32\times32\times(T+T_{FFT+3D+C})=79$ s.

5.2.3. Parallel Reading

3D Depth Resolved Aberrations

Figure 2:
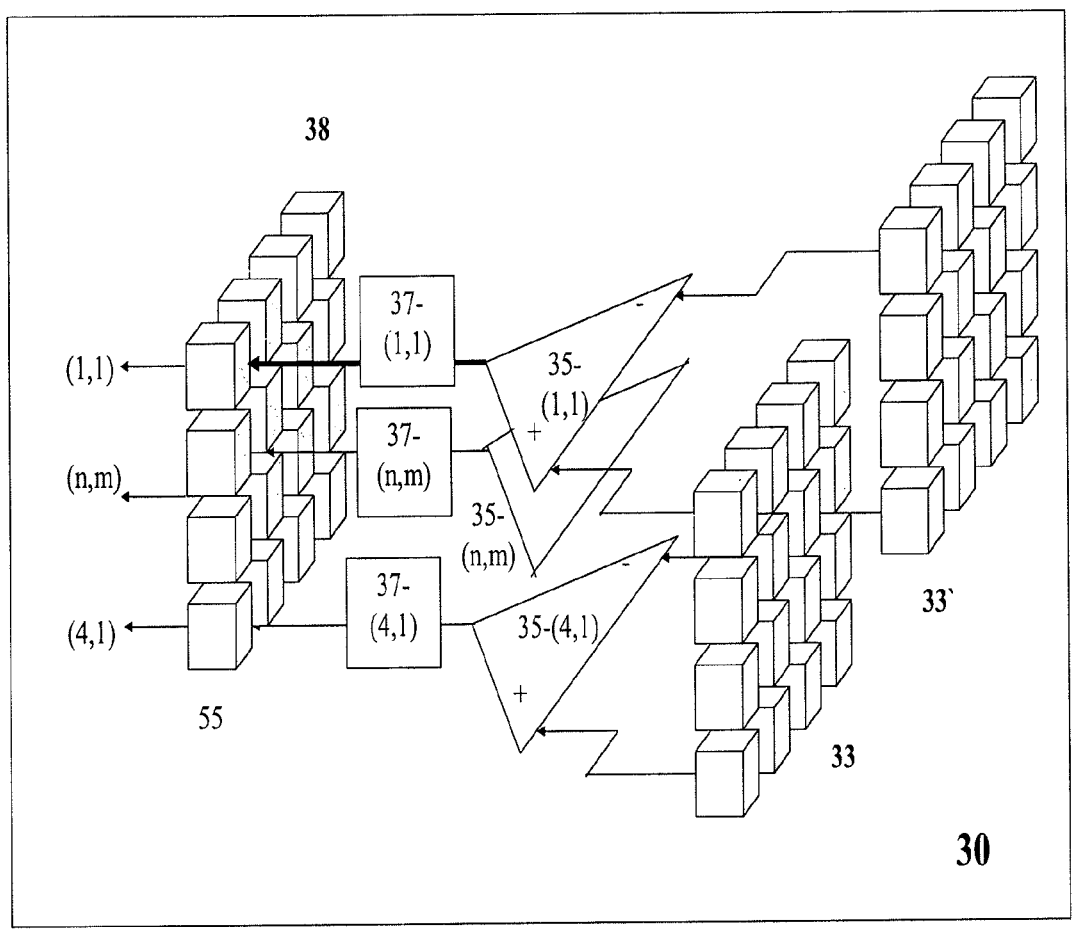
FIG. 2 shows a parallel processing embodiment of the processing block 30 of the CG-WFS.

The bottleneck in the method described above is the speed of reading 2D arrays. The speed of acquisition could be further improved by using a parallel array of photodetectors with independent and parallel reading as array 33 and eventually 33', as shown in FIG. 2. There are now commercially available arrays of 16×16 photodetectors. The block 30 can be equipped with one array, 33, or with two, 33 and 33' in balance detection, where the signal delivered by each (n,m) photodetector in the array 33 is deducted from the signal delivered by the (n,m)' photodetector from the array 33' in a differential amplifier, 35—(n,m). Each such differential amplifier drives a signal processor 37. This can accomplish different functions, such as memory, FFT, band pass filtering or mixing, rectification, and another memory for the result. The signal is then sent to a register or parallel transfer interface, 38, which provides the en-face image of spots, as selected by the coherence gated principle, as signal 39, as labelled in FIG. 1.

Let us say that the frequency of the swept source 1' is swept at 100 kHz (although 500 kHz is already possible). Scanning of all 16 axial depth intervals of 1 mm in the example above now takes as little as T=10 microseconds. Total time for 32×32 repetitions could be performed in T=32×32=10.24 ms. This compares favourably to the exposure time of a CMOS or a CCD camera. For the totality of the digital number of bits for all points in the set of (n,m) out of the 16×16 subarray collected for 32×32 positions on the cornea, identified as (i,j), the time to produce FFT is little. Considering that each photodetector delivers 200 points at 12 bits each and that each such sequence requires 0.2 microsecond as before, then repeating such sequences for 32×32 positions takes 0.21 ms.

5.2.4. A Single En-Face Plane of Aberrations Placed at a Shallow Depth

An even faster rate can be achieved, by wiring the 16×16 parallel array of photodetectors with individual analogue processing channels in blocks 37 in FIG. 2. Each such channel may be equipped with a band-pass filter, or a mixer that mixes the signal with a sinusoidal signal of frequency which determines the number of peaks in the channeled spectrum to be detected. Alternatively, such arrays could be wired up with FPGAs to implement digital signal processing in parallel of blocks 37 and 38. Each channel is equipped with an A/D signal, followed by a digital band pass filter in block 37. All band pass filters are tuned to the same frequency, corresponding to the depth envisaged. For instance, let us say that the tuning rate of the swept source 1' is swept at 100 kHz (although 500 kHz is already possible). Let us adjust the OPD in the WFS interferometer to be OPD ~10 coherence lengths. This will determine ~10 peaks in the channeled spectrum, i.e. the signal on each channel will pulsate at 1 MHz. Modern FPGAs can operate at frequencies close to 1 GHz, therefore a sampling rate of 10 MHz is not unusual for the sampling operation in the A/D converters. For example, with a sampling frequency of 1 GHz, up to 500 MHz signals can be demodulated. At 100 kHz sweeping rate, a signal of 500 MHz frequency is read for 500 peaks corresponding to the same number of coherence lengths. This is equivalent with saying that all 16 channels can be tuned from 2 coherence lengths to 500 coherence lengths each, Using a 100 kHz tuning rate and an OPD to determine 10 peaks in the channeled spectrum results into a maximum 1 MHz frequency signal over one tuning cycle which lasts 10 microseconds. For enhanced accuracy, let us collect 10 cycles, so 0.1 ms required for the 16×16 array to deliver the transversal position of the aberrated spot within the space of 16×16 pixels. A centroiding algorithm finds the $(x_{n,p},y_{n,p})$ position of the center of the spot, where p signifies the axial depth position, $z_p$. This is stored as the slope corresponding to the spatial position (i,j) where the beam is positioned on the cornea and the storing now takes very little, using two registers, each of one Byte.

Such an embodiment can work with a very fast tuning source, as presented in the article "Optical coherence tomography with a stretched pulse supercontinuum source", by S. Moon, published in Optics Express, (2006), 14(24), pp. 11575-11584. This uses a large bandwidth short pulse from a supercontinuum source, which is stretched using a dispersion shifted fiber. Such supercontinuum sources could be driven at 5 MHz but have the disadvantage for OCT imaging that their linewidth is relatively large which limits the OCT axial range. However, this is not a disadvantage here where a shallow fixed depth may be acceptable. Other dispersing means can be used, such as a dispersing compensating fiber, or prisms, or diffraction gratings or fiber Bragg gratings.

To achieve the same performance as that of a commercial WFS based on the SH principle, the CG-WFS should perform the same level of sampling of the wavefront. Using the example of the HASO WFS in 5.2.1 above, the LRT method should be repeated for different values of sampling the cornea, i.e. for 32×32 times for different positions, (i,j) of the incident beam on the cornea, addressed by the galvoscanner 16. Let us now consider that the tuning is at 100 kHz, and 10 cycles are collected, which requires T=100 microseconds. 100×32×32=102.4 ms. This means that at every 102.4 ms, a whole volume of OCT data slopes can be collected, ie a frame rate of approx. 10 Hz to 100 Hz by adjusting the number of cycles collected from 10 to 1. This represents a similar data rate to that achievable by the HASO sensor, with the supplementary advantage that now stray reflections are eliminated and the en-face map of slopes corresponds to a reduced depth of range in the sample. Enhanced sensitivity may also result due to the principle of SS-OCT.

There is another reason for preferring band pass filters. This is because the cube of slopes in 5.2.1 may not represent the real values. All the swept source OCT data for the cube is collected under a certain focus. If aberrations correction for a different depth in the tissue is required, then the data collection has to be repeated with the focus placed at that depth. In other words, the slope information inferred from the cube at a certain depth outside the focus, may not be the same with that obtained by collecting the data when the focus was adjusted to the point of interest.

5.2.5. Chromatic Aberrations

In comparison with prior art methods of LRT/wavefront sensing, the method advantageously can be used to compensate for chromatic defocus, where during the tuning of the optical source 1', a focus change can be altered in synchronism, by actuating on the focusing elements 18, 18' and 18" in FIG. 1 and on the convergence of the incoming beam. Electrical lenses operating at hundred Hz are now available. In addition, the embodiment in FIG. 1 can advantageously provide information on the spectral variation of aberrations.

5.2.5.1. Trade-Off Depth Resolution/Spectral Definition

By restricting the tuning bandwidth, $\Delta\lambda$, less depth resolution is achieved in resolving the aberrations, however better definition of their spectral dependence. The coherence length can be enlarged to the extent to still allow resolving the lens depth from the retina depth. By dividing a normal tuning bandwidth of $\Delta\lambda=50$ nm of swept sources working around 800 nm central wavelength into S=10 spectral windows of 5 nm, the depth resolution becomes approx. $\delta z=0.06$ mm, sufficient to separate OCT signals from the retina from those from the eye lens. S=10 spectral points of aberrations are in this way obtained, with a definition of 5 nm. The aberrations are depth resolved in intervals of $\delta z=0.06$ mm for each spectral window out of S used.

Further improvement of such SS-OCT coherence gate WFS is possible depending on the application. If depth resolved aberration are to be collected, then the process is repeated after moving the focus using 17 to the desired position, collecting all 3D data and inferring the en-face OCT image from same depth where focus was placed.

5.2.5.1.1. Low Cost Swept Source

As an extreme case, let us say that the depth variation of aberrations is discarded. This reduces the demand on the swept source, which could be tuned within a much smaller bandwidth interval. This allows an increase of scanning speed, or the use of lower cost swept sources. A source which can be swept within 1 nm is less expensive than a source tunable within 50 nm. For such reduced tuning bandwidth, a simple laser diode ramped in current may be used.

SH/CG-WFS

FIG. 3 describes a SH/WFS with coherence gating. Light from the object, the retina 101 is sent to a lenslet array 34. The SH/WFS operates by measuring the deviation of the focused spots created by the lenses 34 from a grid of nodes (reference points) defined by the focused spots obtained with an ideal non-aberrated incoming beam, according to means known in the art. The deviation of spots from reference points represent averages of aberrations for a large depth of focus, as determined by the confocal equivalent aperture of the imaging system. Due to the fact that each lens in the lenslet array is very small, less than 1 mm and the focal length of the eye is 2 cm, the confocal depth of focus of each confocal channel corresponding to each lens is several mm wide. Not only that the aberration information is non specific for the depth in the sample, but with such wide depth of focus, the system is susceptible to disturbances from optical elements in the interface optics.

According to the invention, a method and configuration are provided to restrict the depth interval of the aberration information so collected. Here, the aberration information is the slope of the wavefront at the level of each lens in the lenslet arrays 34, where the slope is measured along horizontal and vertical axes from a plane perpendicular on the optical axis. To this goal, an optical low coherence source 1 or a tuning source, 1', is used acid a wide band interferometer, using the optical splitter 2, which splits the light into an object path 10 and a reference path 20. Light from the object path 10, returned from the object 101 is superposed with light from the reference path 20 at beamsplitter 32. Light in the reference path is routed via transmissive loop, mirrors 22a, 23a on the translation stage 21, and in this way, no light is sent back into the low coherence source, known being that such sources are sensitive to feedback. In comparison with prior art SH/WFS devices, the embodiment has the added advantage of balance detection. This contributes to further reduction of non interference signals, such as the optical reflections from different optical interfaces. At the output of splitter 32, the interference signals have opposite phases, signals collected by two cameras 33 and 33'. By subtracting the two camera signals using a differential amplifier 35, the interference signal is doubled and the common mode signal is cancelled, eliminating or at least reducing the stray reflections (including reflections from the cornea when imaging the retina of an eye) as well as the effect of noise and of DC terms in the two beams. In this way, all the dynamic range of signal processors and digitizers driven with output signal 39 can be used for the interference signal variation. The object beam is focused on the photodetector array 33 (33') in a number of spots determined by the lenses in the lenslet array 34, while the reference beam is collimated and covers all the area of photodetectors 33 (33').

Optionally, the configuration in FIG. 3 may be equipped with phase plates and a polarisation beamsplitter, 32, as mentioned before in connection to FIG. 1. Light from the source 1 is linearly polarised using a linear polariser 52. A quarter wave plate, 53, is placed in the object path, oriented at 45 degrees from the incident plane of the linear polarisation, prepared by 52. In the reference path, a halfwave plate, 54, is used to rotate the linear polarisation by 45 degrees. The images of the two cameras are used to provide several facets of polarisation information: a polarisation insensitive measurement, I, birefringence, B, and the rotation of the birefringence axis. I and B could be used to quantify depth resolved aberrations along two orthogonal polarisation axes. This could be used when investigating samples that manifest birefringence. The elements 52, 53 and 54 are optional and therefore are shown in dashed line.

Figure 4A:
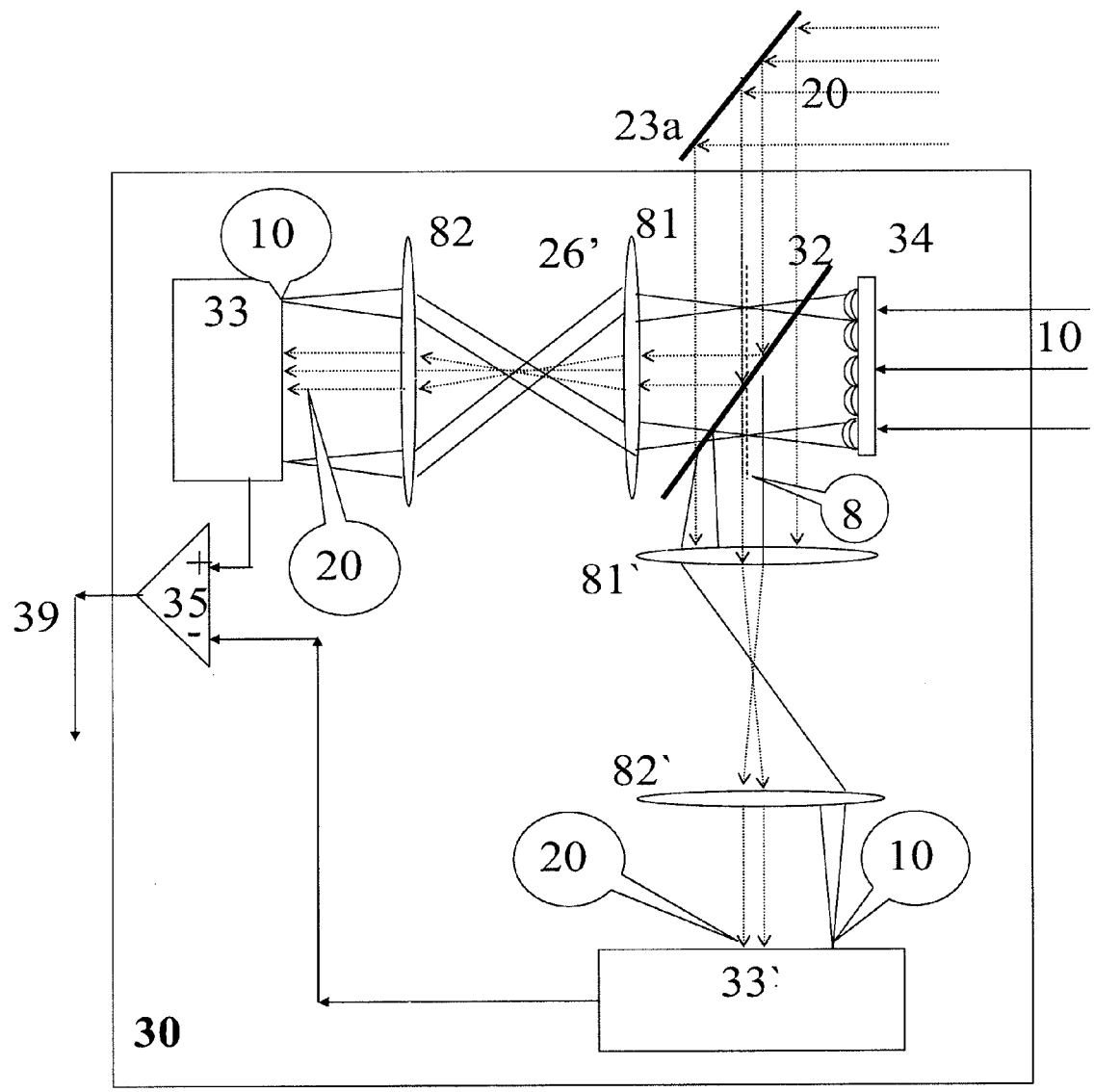
FIG. 4a,b,c. Details of superposing the object and reference beams on cameras.
Figure 4B:
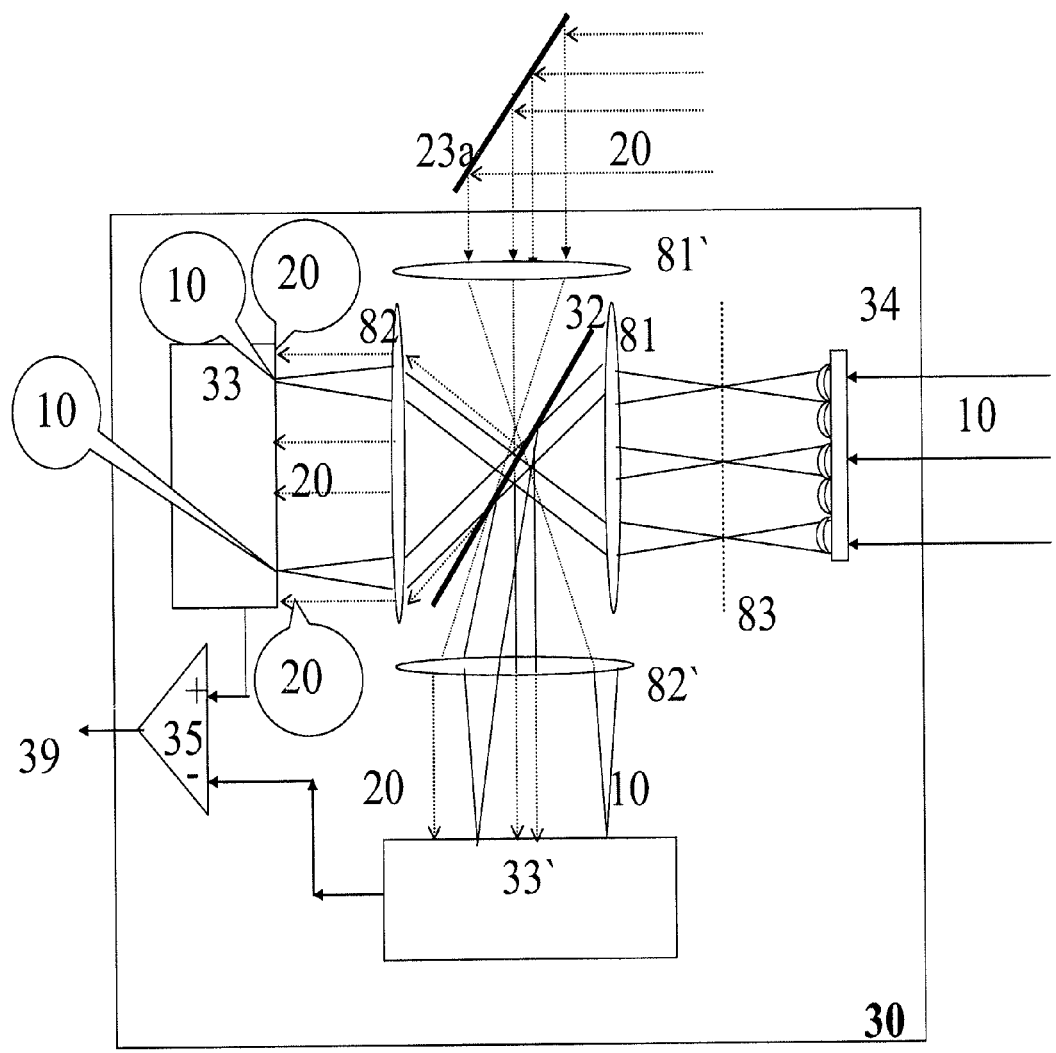

When a large beam splitter 32 is paired with a small focal lenslet array 34, a telescope needs to be used to transfer the two beams to the camera 33, as shown in FIGS. 4a and 4b. In doing so, the telescope arrangement has to accomplish the same function as the schematic embodiment in FIG. 3 where the reference beam 20 (dashed line) is collimated on the photodetector array 33 (and 33' in a balanced configuration) while the beam in the object arm, 10 (solid line) is focused by the lenslet array 34 on the photodetector array 33 (and 33' in a balanced configuration), i.e. the plane of spots, 83, is transferred to the array 33 (and 33'). The main function of the telescope and lenses 81 and 82 is to transfer the spots from the plane of the focus 83 to the plane of the camera 33. The reference beam 20 can be brought to the camera surface either via the same telescope as for the object beam as in FIG. 4a, or by using a lens 81' before the beamsplitter 32, which focuses the light in the front focal plane of the lens 82 (82') in FIG. 4b. In this case, it may be preferable that the beams splitter 32 is set away from the focal point of the reference beam 20 to avoid glare. For instance, 81 and 81' may have a focal length f and 82 and 82' a focal length 3 f, in which case beamsplitter 32 is placed at a distance from lens 82 which is less than 3 f.

The telescope arrangements described in FIGS. 4a and 4b are equally applicable to the LRT embodiment in FIG. 1. They are especially required when lens 18 has a small focal length and the beamsplitter 32 is large.

Figure 4C:
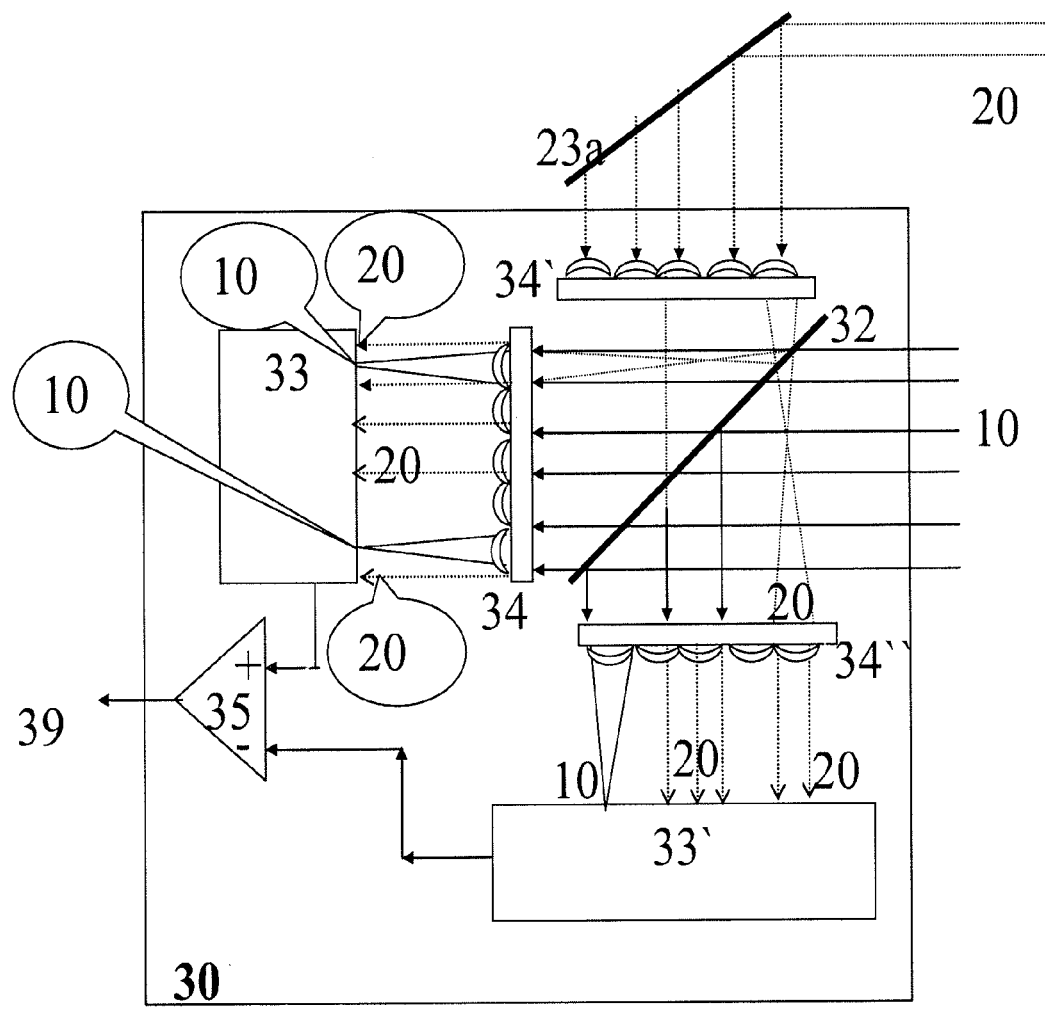

In order to avoid aberrations introduced to the object beam due to the telescope, the configuration in FIG. 4c may be used. In this case, the reference beam is routed by another identical lenslet array, 34', and if balance detection is used, by another lenslet array 34". The lenslets 34' and 34 will convey parallel reference rays towards the sensor 33 whereas lenslets 34' and 34" will convey parallel reference rays towards the sensor 33'. The reference rays are shown in dashed line in FIGS. 4a, 4b and 4c. The distance between the lenslet arrays 34 (34") and 34' is twice the length of the focal length of each lenslet in the lenslet array, allowing for the bulky beamsplitter 32.

If the coherence gated is customised for polarisation sensing, then the beamsplitter 32 is a polarisation beamsplitter.

6.1. Swept Source OCT Based SH/CG-WFS

A first embodiment disclosed is that of a SH/WFS using a swept source, 1'. Spectral OCT using swept sources operates as a longitudinal OCT method. The depth scanning is performed fast by Tuning the laser, 1'. Such tuning can take place at much faster rates than achievable in scanning the depth in TD-OCT. However, the CG-WFS 30 in FIG. 3 and FIG. 4 cannot achieve fast rates of reading due to the limited frame rate of operation of the CCD (or even CMOS) camera 33 (33'). Using a tunable laser source, there is no need for phase shifting interferometry, so in this case, the phase modulator 25 is not required, unless a scheme for eliminating the mirror terms and doubling the depth range is implemented as descried in the paper "Heterodyne Fourier domain optical coherence tomography for full range probing with high axial resolution", by A. H. Bachmann et al, mentioned above. Let us say that the array 33 (and 33') use N×N pixels. The 3D wavefront information can be obtained in the following steps, similar to the procedure described in 5.2. and in connection to FIG. 1 using a tuning source 1'.

1. According to principles known in low coherence interferometry, for each photopixel (m,n) where n=1 to N and m=1 to N, an A-scan is inferred by tuning the laser 1' and acquiring M samples for M different optical frequencies and then performing a Fourier transformation of the M points of the photodetected signal delivered. If the M points collected are not for equidistant values of optical frequency, then a linearization and interpolation procedure, according to means known in the art is used before the FFT. If the source is tuned within an interval $\Delta\lambda$ and M frames are acquired, then aberration corrections are obtained for a depth range of $0.25M\lambda^2/\Delta\lambda$ with a resolution $\lambda^2/\Delta\lambda$.

2. Using the N×N A-scans such collected, a 3D volume, $V_a$ is generated.

3. Then, out of the volume $V_a$, en-face frames are inferred, each containing corresponding deviated spots.

4. In each such frame, deviations of the spots from the on-axis location are evaluated. These determine the aberration information for the given depth value of the en-face frame within the $V_a$ volume of the object.

6.1.1. 3D Depth Resolved Aberrations

To achieve the same performance as that of a commercial WFS based on the SH principle, the SH/CG-WFS should perform the same level of sampling of the wavefront. A commercial SH/WFS such as HASO, produced by Imaging Eye, Paris, uses 32×32 lenslets and for each spot, 16×16 pixels are allocated on the CCD camera. This functionality is achieved with a CCD camera of 512×512 pixels (32×16=512), read at a frame rate of 50 Hz. Normal cameras, 33 can be used to acquire 512×512 pixels at frame rates of F=50 Hz or higher. A 10 µm resolution requires a tuning range of $\Delta\lambda$~26 nm at 800 nm central wavelength. To achieve OPD=1 mm depth range, the number of peaks to be distinguished in the channeled spectrum is given by: $OPD/1_c=100$. The number M of samples should be at least double, i.e. M=200. At a 50 Hz frame rate, this is achieved in a time M/F=4 s. The tuning rate required for the source 1' is to perform a change of $\delta\lambda$~26/200=0.13 nm in 20 ms which can be mechanically achieved, i.e. 26 nm in 200 steps at 50 Hz which requires T=4 s. If faster cameras are used, then a faster tuning rate laser 1' is required.

Transfer time: 12 bits of 512×512 pixels requires 3,150 Mb. Using a 300 Mb rate, the transfer to memory demands 11 ms, i.e. less than 20 ms period for 50 Hz frame rate. By the end of the acquisition, M=200 sampling points are stored for each pixel in the 512×512 array.

These 512×512 reflectivity profiles are then used to assemble a 3D cube of OCT data. Next, p=200 en-face planes can be sliced in the cube, at every 5 microns axial distance, $z_p$ to represent the position of spots corresponding to lateral deviations in the plane of the 512×512 pixels versus axial depth, $z_p$. In each such depth plane, defined by $z_p$, a centroiding algorithm finds the $(n_p, m_p)$ center of the 16×16 pixels, and hence the slope associated to its position.

In this way, depth resolved aberration information is obtained.

In comparison with prior art methods of wavefront sensing, the method can advantageously be used to compensate for chromatic defocus, where during optical source tuning, a focus change can be altered in synchronism. This can be performed controlling the optical element 14. Electrical lenses operating at hundred Hz are now available.

6.1.2. A Single En-Face Plane of Aberrations Placed at a Shallow Depth

Let us say that we are not interested in providing depth resolved aberration, but data similar to a standard SH method, however free of stray reflections. In this case, the number of frames acquired could be reduced drastically and the acquisition time accordingly.

Figure 5A:
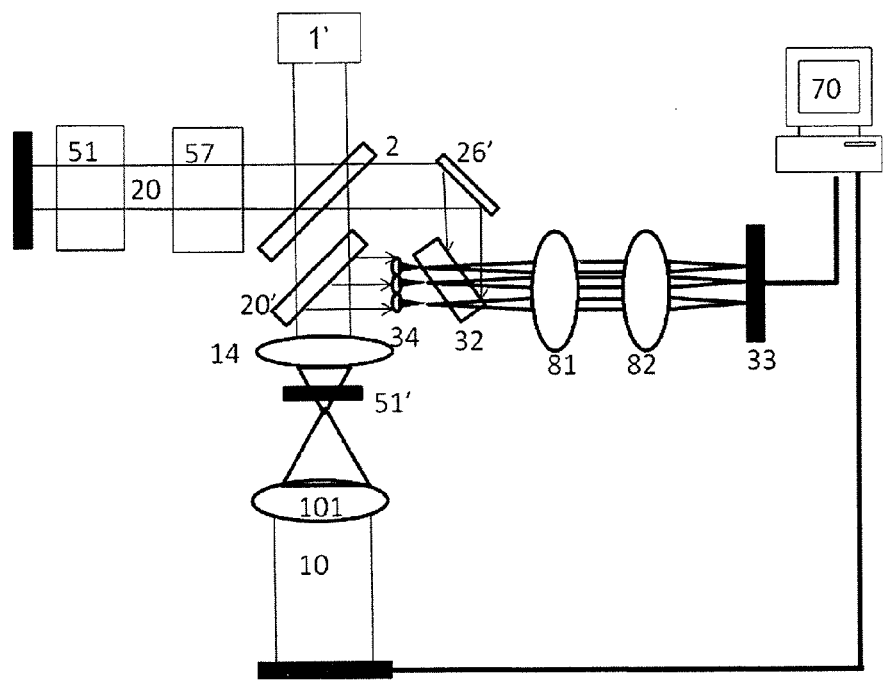
FIG. 5a,b. Practical systems implemented to generate the data in FIGS. 6 and 7.

Preliminary data was obtained using a set-up assembled as in FIG. 3, according to the more detailed diagram in FIG. 5a. Proof of Concept Details of the set-up in FIG. 5a used to demonstrate the principle of operation of a coherence gated wavefront sensor were presented in the article: "Depth-resolved wavefront aberrations using a coherence-gated Shack-Hartmann wavefront sensor", by S. Tuohy and A. Gh. Podoleanu, published in Opt. Express 18, 3458-3476 (2010). The source 1' in the system in FIG. 5a is a Superlum broad sweeper, with a variable sweeping rate of up to 10,000 nm/s, a tuning bandwidth of 50 nm from 820 nm to 870 nm and a linewidth of 0.05 nm. The speed limitation of the system is determined by the CCD, 33, a Retiga-Exi from Qimaging. This is a 12-Bit Camera with 6.45 µm×6.45 µm pixel size.

A high bit rate is required as what we are looking for is the AC fluctuation from the interference over the DC of the light intensity. Limiting the region of interest to 200 by 200 pixels allowed us to run the CCD at a rate of 40 Hz, exposure time 5 ms.

To test the Shack Hartmann coherence gated wavefront sensor, a deformable mirror is used as the sample, 11'. Therefore, in the object arm, achromat lenses 14 and 101 increase the size of the beam diameter from 3 mm to 15 mm to match the diameter of the deformable mirror, a Mirao 52D from Imagine Eyes. Achromat, with focal length of: lens 14 of 30 mm and lens 101 of 150 mm were used.

By actuating on the deformable mirror, the wavefront is altered and the SH spot pattern can be changed. The light then returns through the lenses 14 and 101 and via a beamsplitter 32, passes through the lenslet array, 34, where the light is spatially divided by 90 lenses. The lenslet array 34, is from Welch Allyn, has a focal length of 7.5 mm, with a 200 µm pitch. The lenslet array is optically conjugate to the deformable mirror 11'. Due to the large size of the beamsplitter 32, the CCD array 33 could not be placed immediately after it, therefore a telescope formed from lenses 81 and 82 (achromats of 75 mm focal length each) conveys the focused plane of spots away from 32. After the lenslet array 34, light from the object arm, 10, is superimposed with the light from the reference arm, 20, collimated onto the CCD camera, 33.

To attenuate the signal from the reference mirror 22a and from the deformable mirror 11', neutral density filters 51 and 51' are employed. This is necessary in a configuration as that in FIG. 5a, not only to reduce the power on the sensor 33, but to avoid light being sent back to the optical source 1'. For dispersion compensation, a block BK7, 57, was added to the reference path, 20. To test the capability of the CG-WFS in operating under stray reflections, lens 14 was well centered to create stray reflections on the sensor 33.

The imaging is carried out by treating every CCD pixel as a separate photo detector. As the source 1', sweeps through its tuning range, a number of images are taken. To create the volume, a number of frames are taken. This number defines the depth range of the imaging. The limiting factor of the acquisition is the frame rate of the camera, the desired depth range and the processing speed of the computer. The fewer the number of frames used, the faster the measurement process. However the range of Fourier domain is dependent on the spectral definition, determined by the maximum between: (i) source linewidth and (ii) the step in optical frequency resulting from division of the tuning bandwidth by the number of frames. This means that when the frequency step is much larger than the linewidth, the number of frames determines the depth range. In spectral domain OCT there is also a decay of sensitivity with depth, and this is inverse proportional to the spectral definition. This shows that indirectly, the number of frames limits the range by reducing the signal to noise ratio to nothing for the maximum depth range.

After Fourier transformation, the DC signal is centered at OPD=0. Its width dictates the distance away from OPD=0 that peaks can be resolved, the greater this distance, the larger the number of frames required. Another limitation on the speed of the system is the time taken to process the data. After all the N frames (X,Y) are acquired, they are stored in a 3D array. From this 3D array we then Inverse FFT the data along the N dimension for all values of (X,Y) and place the results into another 3D array with the same (X,Y) dimensions with the N dimension now representing Z. From this it is possible to retrieve an en-face image by software slicing at a selected depth. With a computer (a Pentium 4 2.25 GHz 2.25 GB RAM), it took 1 second to capture N=40 frames and it took 2.1 s to produce an en-face slice from the data cube of 40 images. These durations could be reduced by using a higher performance multiple cores PC or a dedicated DSP board. Linearization was not preformed due to the small number of frames taken.

Figure 6A:
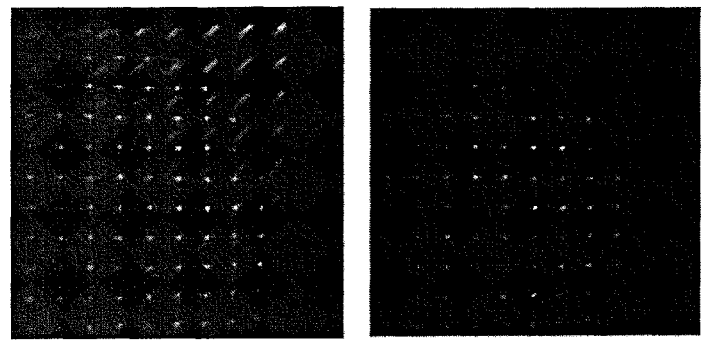
FIG. 6 shows comparatively the spots (a) and one horizontal line through the spot diagram, illustrating the signal to noise advantage (b) created by a prior art SH/WFS and by a SH/CG-WFS based on SS-OCT.

The image in FIG. 6a left shows the CCD image collected with the reference beam blocked (prior art Shack Hartmann wavefront sensor). Stray reflections are visible in the top right as thick diagonal small traces. Right image: OCT en-face image inferred from a stack of 40 frames. Its thickness is less than 20 microns, corresponding to the inverse of the tuning bandwidth. The stray reflections, deliberately generated by lens 14 in FIG. 5a are totally eliminated and slopes can be evaluated undisturbed.

If the tuning bandwidth decreases, this results in an increase in the axial range corresponding to the maximum sampled point. This pushes the peak corresponding to the working OPD to smaller values, proportional to the tuning bandwidth, $\Delta\lambda$. At the same time, the depth resolution worsens, determined by $\sim\lambda^2/\Delta\lambda$. The final result is that the peak corresponding to the given OPD cannot be distinguished from the peak of OPD=0. However, the peak for a larger OPD value can be distinguished from that at zero Hz. This shows that the OPD value has to be suitably chosen depending on the tuning bandwidth and the number of samples. Thus, the number of frames and subsequently the OPD value where the en-face OCT image is inferred from, need to be sufficiently large to separate the peak in the A-scans from the OPD=0 value.

The image in FIG. 6a left shows the CCD image collected with the reference beam blocked (prior art SH/WFS). Stray reflections are visible in the top right as thick diagonal small traces. The bright points represent the spot array of the SH/WFS. The spots in the image represent superposition of spots for a depth interval determined by the confocal channel at the core of each lenslet, which is over 5 mm. Right image: OCT en-face image inferred from a stack of 40 frames. Its thickness is less than 20 microns, corresponding to the inverse of the tuning bandwidth. The stray reflections are totally eliminated and slopes can be evaluated undisturbed. The bright points are of smaller area than in the left image, as they represent a much smaller axial interval in the sample.

Figure 6B:
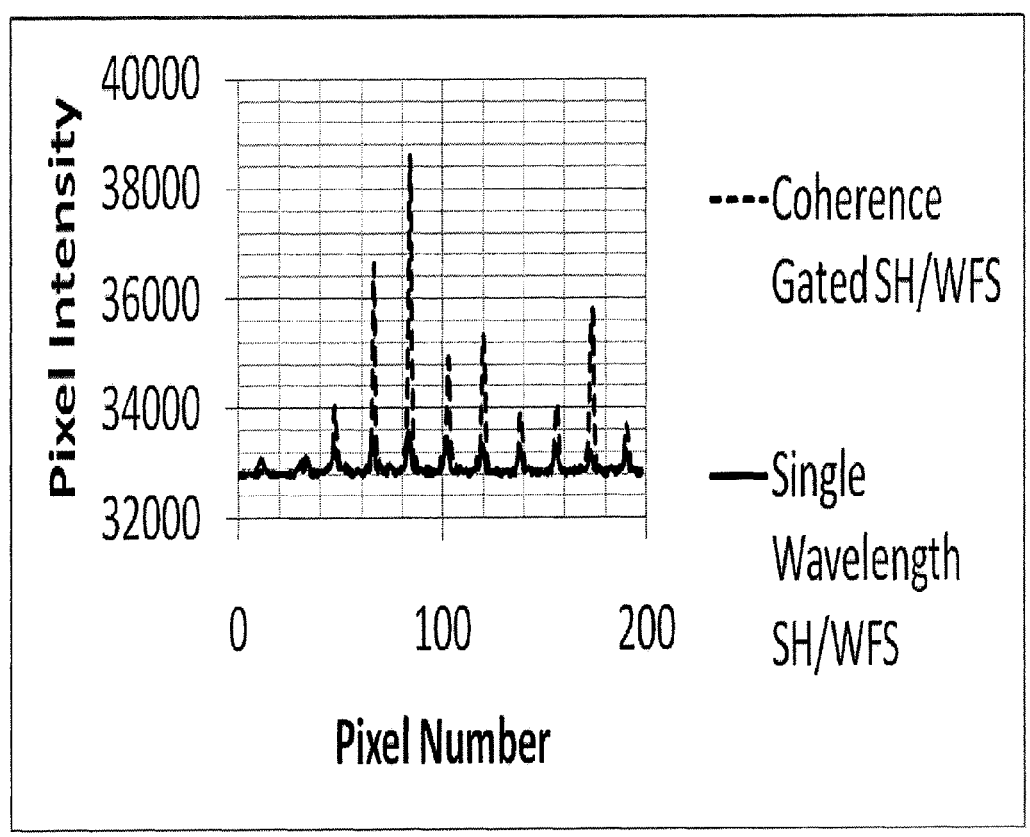

FIG. 6b shows a graph of pixel intensity vs pixel number for an arbitrary line close to the center in both images. The bigger peaks correspond to the case of coherence gated operation, illustrated in FIG. 6a right.

Using a PC Pentium 4, 2.20 GHz, the time taken to create the cube of 40 frames of 200×200 pixels was 2.1 seconds. Such speed is already comparable with speed of prior art SH/WFS. However, working with 512×512 pixels, 200 frames, the Retiga camera operated at 10 Hz, the time to collected 200 frames was 20 s and the time to work out the 512×512 FFTs was 38 s. Such long time can be tolerated in microscopy applications only.

6.1.3. Smart Chip for SS-OCT

Two photodetector arrays which can be read in parallel can be wired pixel by pixel via differential amplifiers 35—(n,m) to provide balance detection for each pixel, (n,m), circuitry which can be incorporated into a field programmable array (FPGA). The diagram of this circuitry is similar to that presented in FIG. 2. Each channel is equipped with a processor, 37, to perform FFT, as explained in 6.1. above, or each channel is equipped with a digital band pass filter to provide directly an en-face image. A processor 38 provides the 3D volume and infers the en-face image of aberrations. In this way, the slow time frame in reading CCD camera is eliminated and a whole volume could be produced fast, at the rate of the swept source. When using a swept source of 100 kHz, with 10 cycles repetition, this gives 0.1 ms. Such a strategy works by using 32×32 smart chips as presented in FIG. 2 followed by reading 512×512 total pixels and using a centroiding algorithm to identify the positions of spots within the global 512×512 en-face frame, for each 16×16 pixels.

6.1.4. Chromatic Aberrations

In comparison with prior art methods of SH sensing, the method advantageously can be used to compensate for chromatic defocus, where during the tuning of the optical source 1', a focus change can be altered in synchronism, by actuating on the focusing element 14 in FIG. 3. Electrical lenses operating at hundred Hz are now available. The embodiment in FIG. 3 can also be used to provide the spectral variation of aberrations.

6.1.4.1. Trade-Off Depth Resolution/Spectral Definition

By restricting the tuning bandwidth, $\Delta\lambda$, less depth resolution is achieved in resolving the aberrations, however better definition of their spectral dependence. By dividing a normal tuning bandwidth of $\Delta\lambda=50$ nm of swept sources working around 800 nm central wavelength into S=10 spectral windows of 5 nm, the depth resolution becomes approx. $\delta z=0.06$ mm, as worked out previously, sufficient to separate OCT signals from the retina from those from the eye lens. S=10 spectral points of aberrations are in this way obtained, with a definition of 5 nm. The aberrations are still depth resolved in intervals of $\delta z=0.06$ mm.

Further improvement of such SS-OCT coherence gate WFS is possible depending on the application. If depth resolved aberrations are to be collected, then the process is repeated after moving the focus to the desired position, collecting the OCT data, producing the 3D volume and inferring an en-face image from the same depth where the focus gate was positioned.

6.1.4.1.1. Low Cost Swept Source

As an extreme case, let us say that the depth variation of aberrations is discarded. If the objective is to eliminate reflections from the cornea, then the depth resolution required for such operation is the eye length. This reduces the demand on the swept source, which could be tuned within a much smaller bandwidth interval. This may result in an increase of scanning speed, or may allow the use of lower cost swept sources. A source which can be swept within 1 nm is less expensive than a source tunable within 50 nm. For such reduced tuning bandwidth, a simple laser diode ramped in current may be used as 1'.

6.2. Full Field Time Domain (TD) En-Face OCT Based SH/CG-WFS

By means of phase shifting interferometry explained in connection with the embodiment in FIG. 1, the spots in the image provided by the CCD arrays 33 and 33' in the SH/CG-WFS are visible only when the OPD between the object arm and the reference arm of the interferometer are matched within the coherence length of the low coherence optical source.

To separate reflections form the cornea and retina, a source with coherence length shorter than 2 to 5 mm is required, and not necessarily an expensive large band source. This allows the use of laser diodes below threshold, of much lower cost than superluminescent diodes. Similar long coherence length values could be sufficient to eliminate the effect of stray reflections from lenses in the interface optics of the imaging system incorporating such a WFS.

The set-up may be equipped which focus capability, provided by focusing interface 14 which can be adjusted using means 15, which could be a mechanical translation stage or the set of 14 and 15 represents an electrical or magnetic or remote adjustable lens. This is a schematic representation, the focus can be implemented by a Badal system as well, or groups of lenses and mirrors by means known in the art and 14 and 15 signify any such possibility of focus correction and controlled adjustment respectively.

Such a SH/CG-WFS can work with lenses in the interface optics, which makes it more compact and simplifies its assembly. For instance, if 14 is a lens or a group of lenses, the reflections from the lenses interfaces do not upset the operation of the depth resolved CG-WFS, as they are outside the coherence gate, as an advantage in comparison to the prior art.

The information provided by line 39 can be used to evaluate the aberrations, which could be presented in the usual way as Zernike coefficients. Alternatively, if the CG-WFS is incorporated into an imaging system, only slope information may be sufficient to correct the aberration, as utilised in the embodiments in FIG. 9 and FIGS. 10 and 11.

A PC equipped with I/O boards, 70 controls the OPD in the SH/CG-WFS interferometer, delivering signal 71 to the OPD adjustment means 21. The PC also delivers controlling signal 75 to the adjustment focus mean 15.

Proof of Concept

Figure 5B:
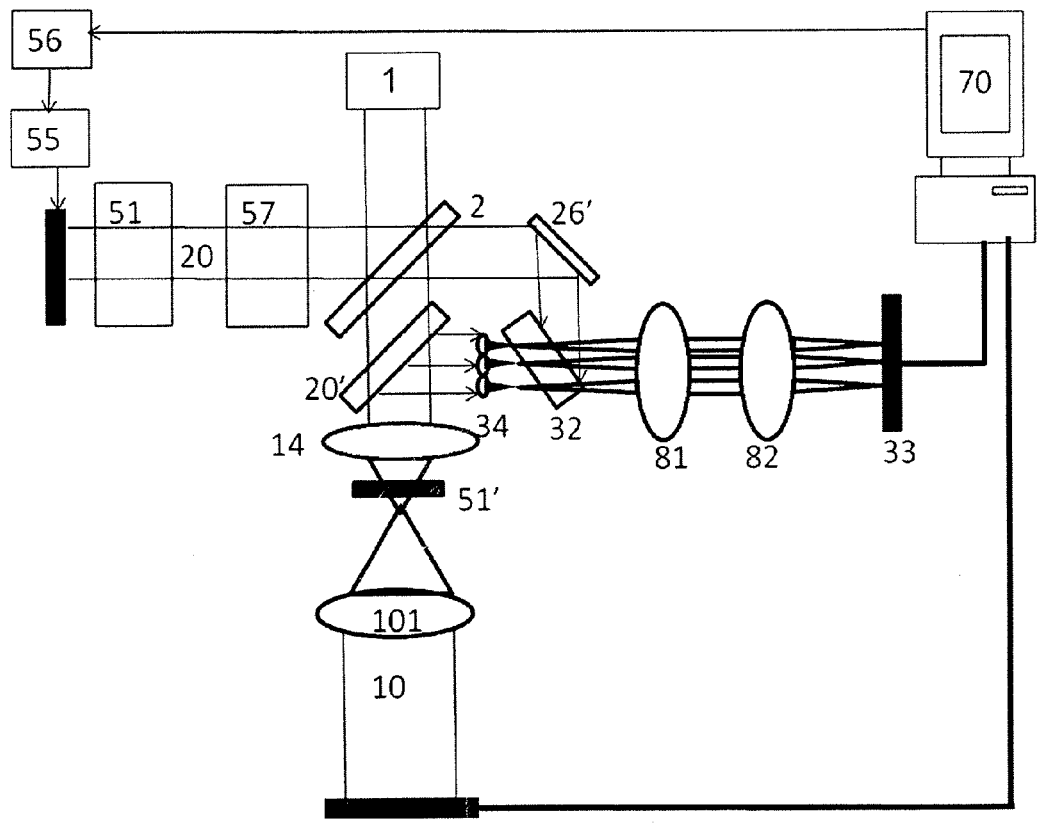

Preliminary results have been obtained using the set-up in FIG. 5b to demonstrate the capability of such a CG-WFS to eliminate the stray reflections in the optics, as presented in the article: "Depth-resolved wavefront aberrations using a coherence-gated Shack-Hartmann wavefront sensor", by S. Tuohy and A. Gh. Podoleanu, published in Opt. Express 18, 3458-3476 (2010). A Retiga-Exi from Qimaging, operating at 10 Hz, which has 12-Bits and 6.45×6.45 µm pixel size as the CCD sensor 33, and a lenslet array, 34, of 90 lenses were used. The source 1 was a Super Luminescent Diode (SLD) with a central wavelength of 831 nm and FWHM bandwidth of 17 nm, which determines a depth resolution of 18 microns. A deformable mirror, 11', (Imagine Eyes Mirao52) was used to create distorted wavefronts. A piezo (Thorlabs AE0505D18 Actuator), 55, was used in the reference arm to alter the OPD in the CG-WFS interferometer. This replaces the stage 21 in FIG. 3, to move the mirror 22a, under the excitation of a generator 56, controlled by the PC 70. Four phase steps were used and a complete en-face OCT image obtained in less than 0.5 s. The generator used to move the piezo, 55, sends a trigger signal to the computer controlling the CCD, 33, to synchronize the image acquisition. Using a Region of Interest it was possible to operate the camera at 40 Hz. The high bit rate is required as what we are looking for is the AC fluctuations from the interference over the DC of the light intensity. The rest of the elements in FIG. 5b are the same as in FIG. 5a.

Figure 7A:
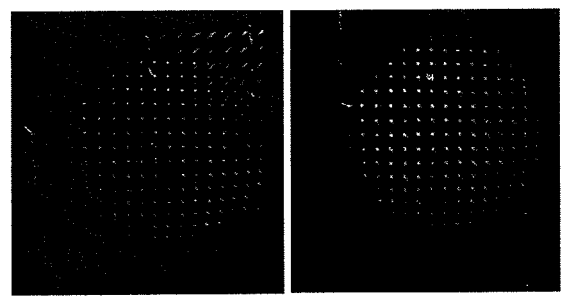
FIG. 7 shows comparatively the spots (a) and one horizontal line through the spot diagram, illustrating the signal to noise advantage (b) created by a prior art SH/WFS and by a SH/CG-WFS based on en-face FF-OCT.

The Piezo 55 is moved to create phase differences equal to $2\pi/N$, where N is the number of images collected during the $2\pi$ cycle at even intervals. Based on principles of phase shifting interferometry, light originating from outside the coherence gate is eliminated and the amplitude of interference from points within the coherence length is recovered. This leaves us with the image from the coherence gated depth interval only. Results are presented here with N=4. The detected intensity on the CCD, is $I_D$:

$$I_D = \sqrt{(I_1(x,y)-I_3(x,y))^2+(I_4(x,y)-I_2(x,y))^2}$$

where $I_N$ are the images taken. Interference is produced between the beams focused by the lenses in the lenslet array, 34, and the reference beam which is collimated and fills an area of 16×16 lenses. The focused beams spread on areas no larger than 4×4 CCD pixels within an area of 32×32 CCD pixels corresponding to each lens in the LA. A centroiding algorithm similar to that used in any SH/WFS was used to identify the position on the CCD of the maximum in each spot. In order to reduce the centroiding errors due to non-uniformity of the reference power distribution across different pixels in the CCD camera, the intensity of the reference beam was first read with the object beam blocked. These values were then used to normalize the interference results before being input to the centroiding algorithm FIG. 7a shows the spots on the CCD camera. The image on the left are with the reference arm blocked and therefore the spots correspond to a standard SH/WFS. Towards the right hand side, the image displays large spots due to the stray reflection from lens 14. The image on the right has been obtained with the reference beam on and after using phase shifting and they represent spatial cropping of spots as determined by the coherence gate. If the reference arm is blocked and the same phase shifting algorithm is applied, no image is obtained. The spots due to the reflections from lens L1 are totally eliminated. The spots due to the object, 11' only are present in the right image. All images have 400 by 400 pixels and the system provided an en-face OCT image of spots (after phase shifting) at 2.5 Hz. However this could be achieved at 10 Hz with 200 by 200 pixels.

Figure 7B:
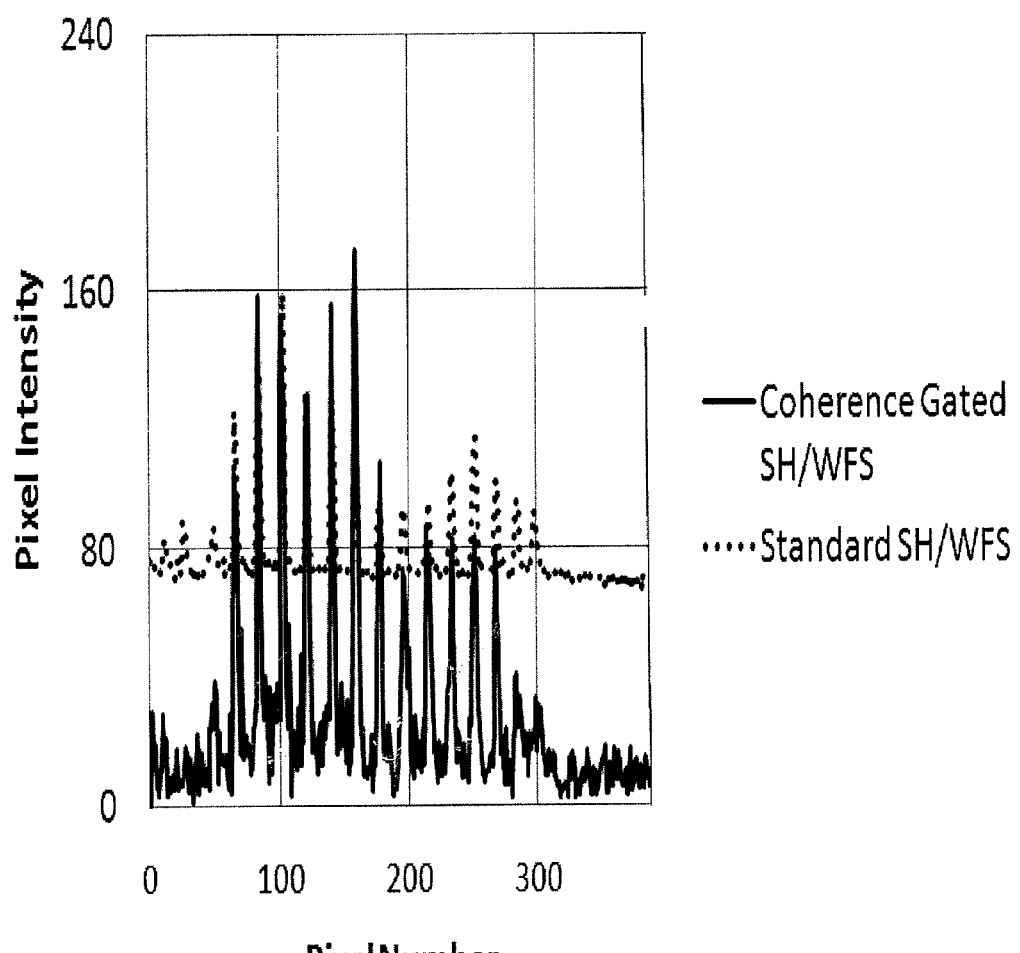

Another advantage of the coherence gated wavefront sensor is that of better sensitivity than the standard Shack Hartmann wavefront sensor due to the interference principle which amplifies the weak signal from the object with the strong signal from the reference arm. This has been quantified in FIG. 7b, which shows graphs of signal versus pixel values collected along one horizontal line through approximately the center of the spot array inferred from that displayed by the CCD camera 33. This illustrates the strength of the signal without reference beam (top) and with the reference beam on and performing phase shifting (bottom).

As a novel regime, according to the invention, the CG-WFS sensor operates with a narrow band tunable laser, where the reading of arrays 33 and 33' is performed after a time $T=RT_{tuning}$, where R is an integer equal or larger than 1. In this way, a TD-OCT regime is implemented despite using a laser source, regime to be advantageously used in the imaging system disclosed at 8.1. below.

6.2.1. Smart Chip for TD-OCT

The main bottleneck in the embodiment above is the photodetector array, 33 (33') in the SH/WFS, which cannot be read sufficiently fast for a good S/N ratio. If all photodetector arrays could be read in parallel, then phase shifting interferometry is not required and much faster phase modulation method could be used. This is possible by using a smart chip, equipped with parallel OCT channels, as shown in FIG. 2 but with a different functionality for the signal processors 37 and 38 than explained in conjunction with the SS-OCT regime employed in 6.1.3. For each photodetector in the array, (n,m), a TD-OCT channel is provided. The phase modulator 25 could be a fast modulator operating in the MHz range. Electrical mixers could be used on each photodetector line, in blocks 37, to demodulate the signal. Smart arrays, as presented in the article "Video-rate three-dimensional optical coherence tomography", by Laubscher, M, Ducros, M, Karamata, B, et al., published in Optics Express, (2002), vol. 10 (9), pp. 429-435 could be used instead of the CCD arrays 33 and 33' to speed up the acquisition by at least a factor of m, due to elimination of m phase shifting interferometry steps. Further increase is possible by using the latest technology of FPGAs inside such smart chips. A complete embodiment, as detailed in FIG. 2, includes two parallel arrays 33 and 33', connected in balance detection via differential amplifiers 35—(n,m), one for each pixel in the array. The output of such differentials is then connected to band pass filters, 37—(n,m) tuned on the phase (or frequency shift) modulation signal applied to 25. Instead of band pass filters, mixers can be used, driven by the same signal as that applied to modulator 25. Thus, parallel OCT processing is performed. Each channel could be read at 1-100 MHz and the extra timing is only required to download in parallel the output signal of the 512×512 channels (as an example of pixel number for comparison with the HASO SH/WFS).

P/CG-WFS

A different embodiment is shown in FIG. 8, where a pyramid wavefront sensor is used. The advantage of the pyramid sensor is that it allows faster data rate in collecting the aberrations than using SH/WFS sensors. Preferably, the pyramid 36 is placed between the splitter 31 and splitter 32, in front of the cameras 33 (or cameras 33 and 33' in balance detection configuration). As with the SH/WFS in FIG. 3, the reference beam is collimated on the photodetector array 33 (33').

The pyramid sensor 36 is schematically represented as one block of what is known in the art, which may include a telescope focusing light on a pyramid, followed by a focusing lens which creates four quadrants of the wavefront displayed on the array 33 (33').

When a large beam splitter 32 is paired with a small operating distance pyramid sensor 36, a telescope need to be used to transfer the two beams to the camera 33 (33'). The principle used is similar to that disclosed in FIGS. 4a and 4b, where a pyramid sensor 36 would replace the lenslet array 34. In doing so, the telescope arrangement has to accomplish the same function as the schematic embodiment in FIG. 3 where the reference beam 20 is collimated on the photodetector array 33 (33') while the beam in the object arm, 10 is focused by the pyramid sensor 36 on the camera (s). The main principle is for the telescope, and lenses 81 and 82 to transfer the spots from plane of the focus 83 of the pyramid to the plane of the camera 33 (33'). The reference beam 20 can be brought to the camera surface either via the same telescope as for the object beam as in FIG. 4a, or by using a lens 81' before the beamsplitter 32.

It should be obvious for those skilled in the art that when a pyramid sensor is used, the beamsplitter 32 may be placed inside the block 36, after the prism part of the pyramid sensor (not shown), before the focusing element of the pyramid sensor (not shown) using an arrangement similar to that illustrated in FIG. 4b for the reference beam or after the focusing element of the pyramid sensor, in which case a set-up similar to that in FIG. 4a should be used to route the reference beam.

The principle described in FIG. 4c can also be used, where the lenslet arrays 34, 34' and 34" are replaced by pyramids.

It should be obvious for those skilled in the art to implement the same principles, as described in FIG. 1, FIG. 3, FIG. 4 and FIG. 5, where the order of different optical components including focusing elements may be different from that shown without departing from the spirit of the invention.

It should also be obvious for those skilled in the art to implement the same principle, as described in FIG. 1, FIG. 3, FIG. 4 and FIG. 5 to any other type of objective wavefront sensor without departing from the spirit of the invention. Other types of wavefront sensors can be customised in the same spirit, according to the examples in FIGS. 1, 3, 4 and 5, to provide depth resolved information of aberrations. Other types of wave front sensors exist or could be devised, such as a distorted grating wavefront sensor or any other type, which could equally be used according to the invention, where coherence gating is incorporated into the wavefront sensing process. With this goal, a reference beam could be added via a controllable path length reference path to any wavefront sensor and using different principles of low coherence interferometry, TD-OCT, SS-OCT or FD-OCT (using a spectrometer and a broadband source, not shown) to apply coherence gating to select the depth within the object volume, tissue or microscopy specimen where the WF is collected from.

The depth resolved wavefront sensors according to the invention presented above, could serve vision research or microscopy on their own.

Combined Imaging Systems with CG-WFS

According to a different aspect of the invention, methods and systems are presented which incorporate depth resolved wavefront sensors into retinal or microscopy imaging systems to improve their resolution. According to the invention, CG-WFSs could be used in combination with imaging instruments, operating according to optical coherence tomography (OCT) or scanning laser ophthalmoscopy (SLO) or confocal microscopy (CM) principles, any other type of microscopy such as phase microscopy, or multiphoton microscopy (MM) as explained below in connection to the embodiments in FIGS. 9 and 10.

As seen in FIG. 9, a depth resolved CG-WFS, 30 is used in conjunction with an OCT channel OCT, 40, or with a CM (SLO, or MM) channel, 60, or with two or more of such channels operating simultaneously. The CG-WFS can work as the Shack-Hartmann WFS in FIGS. 3 and 4 or as a pyramid sensor in FIG. 8. Light from the broadband source 1 or from the tuning source 1' is sent via the splitter 2 along the object path 10 and along the reference path 20. In the object path, a deformable mirror 11 is provided under the wavefront sensor (WFS) control, 30, which outputs signal 39 to the driver 50 of the corrector 11. Mirrors 12 and 13 are used to ensure that the beam has an incidence close to normal on the deformable mirror 11, to reduce the astigmatism. A translation stage 15 is used to adjust the convergence of the beam being sent to the eye 100 whose retina, 101 is to be imaged, by moving a focus element 14 axially. This is a schematic representation, the focus can be implemented by a Badal system as well, or groups of lenses and curved mirrors by means known in the art and 14 and 15 signify any such possibility of focus correction and controlled adjustment respectively. The light is transversally scanned by XY scanner 5 and conveyed to the eye via interface optics 6. The blocks 5, 6 and 14 are shown separately, however they could be interleaved, like the line scanner, a galvo mirror, a polygon mirror, a piezo, an acousto-optic deflector, etc, followed by lenses or curved mirrors, and then by a frame scanner consisting of one of the possible means of scanning known. The scanner block 5 here tilts the beam through the eye pupil, different from the LRT method in FIG. 1, where the scanner 16 translates the beam parallel to itself before falling on the cornea. The same source beam is advantageously used for providing reference to the wavefront sensor 30 as well as for imaging. The interface optics 6 and focusing element 14 could use lenses because reflections from their surfaces do not disturb the coherence gated wavefront sensor as it happens in the prior art. Splitter 26 divides the reference beam into two optical paths, one reference path, 20a, for the low coherence interferometer in the wave front sensor 30 and the other for the OCT imaging instrument, 20b. Two optical path difference adjustments are shown for the two interferometers, in the WFS and OCT, using translation stages 21 and 27. Mirrors 22a, 23a, 22b and 23b are used to route the reference beams, in the two reference paths 20a and 20b respectively. Light from the retina, 101 returns via interface optics 6, transversal scanning system 5, correction path via mirror 13, corrector 11, mirror 12, splitter 2 and is divided by splitter 31 into two signals, one along the CG-WFS path, 10a, and the other along the OCT path, 10b.

Light along path 10a is sent to the block 30, consisting of at least a splitter 32, a lenslet array 34 and a 2D photodetector array, 33, a CCD, or a CMOS camera or a smart chip 2D array, as detailed in FIG. 2. The object light along path 10a creates multiple spots in the lenslet 34 which are projected onto the photodetector array 33 where they interfere with the reference beam from reference path 20a.

Balance detection could also be implemented in the CG-WFS, with two photodetector arrays, 33 and 33', whose signals are deducted in a differential amplifier 35, in a replication of the schematic embodiment in FIG. 3 or detailed embodiment in FIGS. 4a and 4b. After the differential amplifier, 35 (or many such lines in the parallel processor in FIG. 2), CG-WFS signal 39 is provided which via the control block 50 delivers the correction signal to actuate on the wave front corrector 11.

If the beamsplitter 32 is large and the focal length of the lenslet array 34 is small, then an arrangement as that disclosed in FIG. 4a, 4b or 4c can be used, as described above in conjunction to FIG. 3. In this case, rays 10 and 20 in FIGS. 4a, 4b and 4c should be replaced by rays 10a and respectively 20a.

The light along path 10b is sent to the splitter 41 where it interferes with the OCT reference beam along path 20b and balance detection is implemented using photodetectors 42 and 42' and a differential amplifier 44, providing OCT signal 49. Such signal processing is typical for time domain OCT and swept source OCT.

Again, as with the Shack-Hartmann embodiment in FIG. 3 and Pyramid embodiment in FIG. 8, the reference beam 20a needs to be collimated on the array 33 (33') and different arrangements are feasible as disclosed in FIGS. 4a, 4b and 4c.

A PC equipped with I/O boards, 70 controls the OPD in the OCT and in the CG-WFS interferometers, delivering signal 71 and 77 to the two OPD adjustment means 21 and 27 respectively The PC 70 may also deliver controlling signal 75 to the adjustment focus mean 15 and controlling signal 76 to the XY transverse scanning means, 5.

An SLO or a CM, or a MM channel is provided, 60, if a splitter 61 is introduced into the path 20a as shown, which diverts some of the light towards a highly sensitive SLO, or CM, or photomultiplier receiver, 62, which produces the SLO or CM, or MM signal, 69. The receiver 62 may also be equipped with optical filters to separate auto-fluorescence signal, as generated by the target 101, or to sense the fluorescence of a drug placed in the sample 101, or to select the two photon fluorescence, or select a harmonic of the optical excitation signal generated by the sample 101, in typical experiments of multiphoton microscopy (MM). The embodiments in FIGS. 9 and 10 could work with OCT, CM (SLO) or MM channels simultaneously, or could be equipped with channel OCT, 40, or channel SLO (CM), or MM channel 60, only. The CM channel at the core of the OCT channel could also be used to provide the CM (SLO) channel without resorting to a separate SLO (CM) channel. To this goal, the photodetector signals provided by photodetectors 42 and 42' are summed in the adder block 44' to provide a CM (SLO) channel 69'.

En-Face TD-OCT CG-WFS

In this case, unique for such dual channel OCT/SLO or OCT/CM embodiment is that the depth wherefrom the aberration is collected from using the WFS 30 is similar to the depth where the signal is collected by the OCT channel, 40 and by the SLO (CM) channel 60, keeping in synchronism the coherence gate via adjusting means 21 and 27 and focusing means 14 and 15.

Spectral Domain OCT Based CG-WFS

In this case, the imaging system and the CG-WFS operate independently. After 3D depth resolved aberrations are acquired, the imaging system (OCT, CM, or MM or all) can be actuated to capture images under adjustments corresponding to a given depth as inferred by the CG-WFS from a desired depth in the volume of data captured by the CG-WFS.

Different Possible Combinations

According to an additional aspect, the invention provides protocols for using the combination of CG-WFS and imaging channels with different regimes of operation for the CG-WFS and for the OCT method employed in the OCT channel. Several possibilities exist, where the OCT imaging channel can operate in either time domain or spectral domain OCT and the WFS can be any of the LRT, SH, pyramid, or any other WFS principle and based on any coherence gated principle. They could work simultaneously, via the same interface optics, using the same source or different sources, where the two systems share a dychroic splitter. The two channels may also operate sequentially. Several such combinations of operation regimes are detailed immediately below.

Ideally, aberrations should be acquired for each angular direction of the beam going through the eye pupil (or microscope objective 102 replacing the anterior chamber), i.e. for each pixel within the image, $(x_i, y_j)$ and for each depth $z_p$. This requires a large number of data sets which demands a long acquisition and processing time. However, depending on the variation of aberrations, transversally or axially, different simplified protocols can be adopted.

8.1. SS-OCT Imaging and TD-OCT SH/CG-WFS Using the Same Swept Source 1'

Let us consider the example above of a swept source being tuned at F=100 kHz. This means that a set of A-scans for 256×256 tilt values of the transversal scanner 5 are acquired in $T_{3D}$=0.66 s. Using the balance receiver 44, a 3D cube of swept source data is captured in $T_{3D}$. The arrays 33 and 33' in the SH/CG-WFS integrate the signal during the tuning, therefore if their integration is adjusted to 1/F=10 microsecond, the signal delivered is that of a TD-OCT operating around OPD=0. Therefore, despite tuning a narrow band laser, the WFS operates according to a TD-OCT principle. To operate properly, without mirror terms, the depth where OPD=0 in the OCT imaging interferometer is adjusted via 27 in front of the tissue. On the other hand, if the interferometer in the CG-WFS operates in TD, then the OPD should be adjusted, via 21, to the depth in the tissue where aberrations are to be inferred from (i.e., for OPD=0). This shows that the two OPDs have to be different if different regimes of operation are employed, time domain and spectral domain in the two channels, imaging and CG-WFS.

8.1.1. TD-OCT Based CG-WFS Operating at the Same Frame Rate as the Line Rate of the Swept Source Let us say that the arrays 33 and 33' can be read at F. During the interval 1/F, all optical frequencies are swept. If a frame is acquired with a first phase step in the WFS interferometer, and repeated for two subsequent steps, then using phase shifting interferometry, an en-face OCT image of the aberrated spot position at the depth corresponding to OPD=0 as sampled by the position of the translation stage 21 is obtained, as explained in 6.2 above for every set of three lines in the image corresponding to three frequency scans of the optical source. This can provide much more correcting points per image frame than in 8.1. However, this regime would require CMOS arrays to operate at 100 kHz. A frame rate of 10 kHz is more achievable, in which case the integration takes place over 10 scanning lines. Considering three phase steps, at every 30 lines, an en-face image of the spots is produced, with information updated at 0.3 ms. Within a frame of 300 OCT lines, 10 such updates of the wavefront corrections can be performed.

In this way, the imaging process is operated under WFS correction acquired over the previous 30 scanning lines.

8.1.2. CG-WFS Operating at a Frame Rate Equal to $T_{3D}$

A more relaxed operation of the CG-WFS is possible by providing an average correction to the corrector 11, over the whole transversal positions of the object beam. As explained in 8.1.1, imaging proceeds in steps of $T_{3D}$. Each OCT imaging step, consists in collecting the 3D data, in a time $T_{3D}$. A different phase shift is applied to the CG-WFS according to 6.2, for each such step. After 3 such steps, starting from the $4^{th}$ step, an en-face mapping of the spots is obtained which can be used to control the AO loop. For every set of three imaging steps, three phase shifted frames are acquired in the CG-WFS and correction evaluated, similar to the procedure explained in 6.2.

8.1.2.1. Subdivisions of $T_{3D}$

For the first ⅓ of the $T_{3D}$, according to 8.1.1. equal to 0.22 s, a first phase shift is applied, for the next 0.22 s, the second phase shift and for the last 0.22 s the third phase shift. In this way, in the same interval $T_{3D}$ of acquiring the 3D OCT imaging data, all three phase steps are also acquired by the CG-WFS. This allows the OCT acquisition to operate at the very high rate of the tuning, 100 kHz, finalise all imaging in $T_{3D}$=0.66 s and update the aberration correction at every $T_{3D}$=0.66 s, and not at $3T_{3D}$ as above.

Both procedures above acquire 3D OCT data under a depth resolved aberration correction corresponding to a depth selected by the OPD=0 in the WFS interferometer. This could be at the top of the retina, or deep into the retina. The method according to the invention not only can select which layer in depth to be visualised with best AO correction, but eliminates the stray reflections which otherwise would have disturbed the prior art SH/WFS. This allows the use of lenses in the interface optics, shown by lenses 14 and 6, which can lead to a more compact AO layout.

8.2. Flying Spot En-Face OCT Imaging and En-Face FF-OCT Based CG-WFS Using the Same Large Band Optical Source for Both the WFS and the OCT Channels In TD-OCT, en-face imaging is possible without phase modulation, using the path modulation created by the transverse scanners as explained in the U.S. Pat. No. 5,975,697 to A. Podoleanu and D. A. Jackson. For the WFS however, which uses the CCD arrays 33, or 33 and 33', phase modulation is required. For each depth in the object 101, at least three frames are acquired with the CCD array 33 or arrays 33 and 33' for three phase shifts imprinted by the phase modulator 25. More steps m could also be applied according to means known in the art of phase shifting interferometry.

For en-face OCT imaging, to generate a C-scan (constant depth) image from a certain depth in the object, at OPD=$z_p$, aberration correction needs to be inferred from the WFS sensor at that depth. A simplifying protocol is collecting the aberrations in a first step and imaging performed in a second step, where the imaging in the OCT channel can take place using a stored set of aberration corrections. Such set of aberrations can be stored for each depth. Then the OPD is changed in the OCT interferometer and a new set of corrections are applied corresponding to that depth.

In a further simplifying step, the correction process itself is simplified, aberrations are acquired for the beam on-axis and applied for all transverse pixels $(x_i, y_j)$ within an en-face frame. This is applicable when the aberrations do not vary significantly transversally, i.e. across the pixels in a frame but vary more from depth to depth.

A higher resolution image can be produced if for each pixel within the en-face image (OCT, CM, or MM), a depth resolved aberration correction is applied from the library of aberrations at the same depth, but for different angular positions of the beam through pupil 102 when imaging the retina, or for different positions of the beam on the microscope objective 102 when imaging a sample in microscopy (confocal or multiphoton microscopy using nonlinear optics and a short pulse high power optical source 1). For P×P pixels in the image, this requires $P^2$ sets of aberrations for each depth.

Using en-face OCT to generate a B-scan (cross section) image, at each advancement of depth, new corrections are applied from the stored set of aberrations corrections for that depth in the object. In this case, only P aberrations are required from the stored data, corresponding to the fixed vertical position of the beam along a fixed y coordinate, corresponding to j=J, and considering a B-scan image produced along lateral pixels $(x_i, y_j)$.

8.2.1. Fourier Domain (FD) OCT Imaging and En-Face FF-OCT Based CG-WFS Using the Same Large Band Optical Source for Both the WFS and the OCT Channels The imaging system could also operate based on principles of Fourier domain (or channeled spectrum)—OCT, using a spectrometer to read the output of the OCT channel, as disclosed in the application US20070165234, Spectral interferometry method and apparatus. In FIGS. 9 and 10, one or both of the photodetectors 42 and 42' are replaced with spectrometers. Usually, one spectrometer suffices, in which case the beamsplitter 41 preferably is different from 50/50, allowing more of the object signal than of the reference signal. Balance detection of spectrometers is also possible, in which case the beamsplitter is 50/50. The spectrometer (s) can be implemented using a linear CCD or a 2D CCD camera behind a prism or a diffraction grating.

Usually, FD-OCT can produce an A-scan at tens of kHz, i.e. much faster than the CG-WFS. A simplifying protocol is collecting the aberrations in a first step and imaging performed in a second step, where the imaging in the OCT channel can take place using a stored set of aberration corrections.

In a further simplifying step, the correction process itself is simplified, aberrations are acquired for the beam on-axis and applied for all transverse pixels $(x_i, y_j)$ within the B-scan OCT image generated by FD-OCT. This is applicable when the aberrations do not vary significantly transversally, i.e. across the pixels in a frame.

8.3. En-Face FF-OCT Based CG-WFS Using a Broadband Source 1 Followed by SS-OCT Using a Tunable Source 1'

1. The block 30 is used to collect corrections at every pixel (i,j) in the object plane and the variation of aberration with depth in the retina is ignored. For this goal, the source 1 needs a coherence length sufficient to eliminate the reflections from the anterior chamber. To integrate over all layers in the retina, a coherence length shorter than 5 mm looks appropriate. Using phase shifting interferometry, corrections are collected for all $P^2$ pixels. For a frame rate F, the time required is m/F, where m is the minimum number of phase shifting interferometry steps, m=3. With F=30 Hz, an en-face image is produced at 10 Hz. For $P^2$=32×32 positions of the steering object beam through the pupil, 100 s are required. If in a $1^{st}$ step, corrections are collected to correct a B-scan image in the next step, then only P=32 samples are required, so $mPF^{-1}$=3 s which becomes more amenable with the eye movements.

2. Then, the optical source, 1, is replaced by the tunable laser, 1', and fast imaging is now feasible, at the rate allowed by the SS-OCT principle. Line rates of f=20 kHz are easily achievable for SS operating in the 800 nm for imaging the retina. A B-scan image of P=1000 transversal pixels is obtained in $Pf^{-1}$=50 ms. To keep the data rate fast, it may be acceptable that the correction is updated 32 times within a transversal line of 1000 pixels, using the stored values obtained in the first step.

A further possibility, is to use the elements of the WFS, in block 30, in two regimes of operation. For instance, if a fluorescent tag is used in the sample 101 to provide the guiding star beam for the WFS correction, then the block 35 is switched to summation instead of difference (or only one camera, 33 or 33') is employed and the path 20a is blocked.

To block the reference path, block 51 can be used, where the attenuation of the filter is momentarily adjusted to a very large value, in which case a controlled liquid crystal attenuator can be used to vary the attenuation between the two regimes of operation: (i) standard (no interference), infinite attenuation and (ii) with interference, attenuation adjusted to avoid saturation of the array. Alternatively, a simple screen 58 can be inserted into and out of the reference beam as shown by the double arrow (dashed line) in FIG. 9.

Block 30 implements the traditional operation of a SH/WFS. Then, block 30 can be switched to implementing the regime of a coherence gated WFS, where 35 is used differentially and reference power is applied from the reference path 20a to the splitter 32. In this case, the block 30 implements a dual path measurement, working in reflection, in opposition to the previous regime of operation, where the WFS was sensitive to one way aberrations, those from the sample, 101, towards block 30 only. Such dual regime of operation is only possible by the current disclosure. By combining the information such collected, the aberration of the exciting path, from the system towards the point in depth in the sample could be inferred. Such information is useful in the operation of the MM channel, where essential is to compensate for the aberration in the excitation path, to create the best focus of the excitation power, while the resolution in the fluorescence channel is not that important (i.e. aberrations in the path from the sample towards the imaging system can be ignored).

8.4. SS-WFS and SS-OCT Using the Same Swept Source 1'

SS-OCT is an A-scan based OCT method and operates under fixed focus. Therefore, such an embodiment is useful when the variation of aberrations in depth in the object is less significant than the transversal variation of aberrations. This protocol and embodiment is useful in AO based OCT and SLO imaging of the eye, where the depth resolved WFS in FIG. 9 does not target providing depth resolved aberration from within the object, the retina 101. In this case, imaging can take place under a fixed aberration correction value, as inferred from the on-axis position of the object beam, value then used for all the pixels along the transversal direction in the B-scan (cross section) OCT image. This information may be collected from one depth, such as the retinal pigment epithelium, or from an integral of depths, such as all backscatters along the ray in depth within the retina thickness. In this case, what is provided in comparison to prior art is aberrations devoid of stray reflections from the object arm. In other words, the depth resolution of the CG-WFS is poorer than the retina thickness but better than the separating interval between the retina and the position in depth where the stray reflection originates from.

Alternatively, if P aberration corrections are acquired in the measurement of the wave-front for P pixels, $x_i$, along the transversal direction at a fixed Y, they could be applied for each new position, $x_i$, of the object beam in the imaging process.

As a peculiar case, the tuning range of source 1' when collecting WFS aberrations could be different from the tuning range when acquiring OCT images. A smaller tuning range for WFS step is required, just enough to eliminate the stray reflections from the optics interfaces and the cornea for instance when imaging the retina. Then, in the imaging step, the maximum tuning range should be employed to achieve the highest depth resolution.

8.5. LRT Based CG-WFS Combined with an Imaging Instrument

Such a combination is shown in FIG. 10. Two separate scanners are used by the imaging instrument, 5 and by the CG-WFS, 16. The imaging scanner, 5, tilts the beam through the eye pupil, 102, using the converging elements 17 and 17'. The CG-WFS scanner 16, moves the beam parallel with itself. Preferentially, the CG-WFS operates fast, based on the SS-OCT principle, using a parallel array of photodetectors as disclosed in 5.2.3, using the embodiment in FIG. 2, therefore a swept source 1' may be used via splitters 26 and 26' and mirror 26". The imaging instrument can use the same source, but conveniently, a different source may be used, of different wavelength, 1'$a$, (dashed line) to reduce the attenuation of light in the splitters 19 and 19', by employing dychroic filters, or hot or cold mirrors. Splitters 26 and 26' can be removed and 260 and 260' used instead, shown for convenience of sketching in FIG. 10, a single splitter may suffice to send light towards mirror 22$a$. For instance the imaging system can operate on 800 nm while the CG-WFS in visible or at a longer wavelength, in which case the arrays 33 and 33' use InGaAs photodetectors. The OCT system can operate as TD or SS-OCT using respectively a broadband source 1 or a swept source 1'. For multiphoton microscopy, a source 1" emitting femtosecond high power pulses is used and the two photon fluorescence, three photon fluorescence or second or higher order harmonics produced by the sample or by chemicals inserted into the sample, are processed by receiver 60, equipped with a suitable filter.

8.5.1. Both Systems Driven by the Same Swept Source, where the CG-WFS Operates in Time Domain If losses on splitters 19 and 19' can be kept low, with high sensitivity of the arrays 33 and 33', then the same swept source can be used for both systems. A swept source at 0.5 (5) MHz can allow fast operation of the CG-WFS and sufficient integration over a 1 ms line rate in a TD en-face OCT imaging system. For 500 pixels at 1 ms, 2 microseconds are required for each pixel in the en-face OCT image, if the whole bandwidth is scanned within such interval, then the OCT operates like in time domain. A sweeping rate of 0.5 MHz ensures such an integration time per pixel, while 5 MHz swept source leads to 10 cycles per en-face pixel. The supercontinuum source using stretched pulse in dispersion shifted fiber (at 5 MHz line rate as presented in the paper by Moon published in Opt. Express mentioned above) can be successfully employed as a large bandwidth source in the OCT system, in which case the sensors 33 and 33' employ fast InGAsAs photodetectors and the block 30 operates with a smart chip as in 5.2.3. and in FIG. 2 at GHz rate (although Moon paper refers to 1300 nm, the principle is expected to be proven for shorter wavelength). Frequency sweeping is essential for the CG-WFS channel while is discarded in the TD-OCT channel.

8.5.2. Separate Sources Using a Common Pulsed Supercontinuum Source

The inset 110 in FIG. 10 is a block source which delivers a broadband beam at output 1 and a swept spectrum beam at output 1'. A supercontinuum femtosecond source operating at a sufficient high repetition rate, 111, sends short pulses into a dispersing element, 112, such as a dispersion shifted fiber, dispersion compensating fiber, groups of prisms or/and diffraction gratings or fiber Bragg gratings and produces a swept frequency interval, as any swept source 1'. A stretcher 113, such as a long single mode fiber, enlarges the pulses sent to the output as a broadband source 1. The output 1 can be used for TD-OCT in the imaging OCT channel while the output 1' can be used for CG-WFS operating on SS-OCT principle. The pulses from the emitter 110, if short, such as femtoseconds, are sent to output 1" to be used in a nonlinear optics microscope, operating on multiphoton interactions, to be sensed in block 60.

A possible application for fast tuning swept sources with not so narrow linewidth, is that of providing chromatic aberrations. The tuning time of 2 microseconds is divided for instance in S=10 temporal windows which determines 10 spectral subintervals. Each such temporal window delivers aberrations corresponding to the middle of the tuned bandwidth in each such S temporal subintervals.

If the imaging instrument is based on multiphoton absorption, for instance two photon absorption (2PA) for microscopy, the optical source 111 emits very short pulses, of high power. En-face imaging is obtained based on the 2PA excited fluorescence. The aberrations in the focus volume are corrected based on a CG-WFS operating on swept source principle, as described above, where the CG-WFS is excited by a dispersing element, such as a dispersion shifted fiber which stretches the pulses of the optical source 111, obtained from the output 1' of block 110.

This principle of operation described here for the LRT/CG-WFS and for its combination with imaging channels can be extended to the SH/CG-WFS, where the SS-OCT principle is used, a lenslet array, 34, is added and the photodetector array 33 (33') is replaced with a parallel array of photodetectors.

The multiple output source 110, as shown by the inset in FIG. 10 can equally be applied to the embodiment in FIG. 9, to provide short pulses for multiphoton microscopy using the pulses from 1" while employing the CG-WFS in time domain using the output 1 or operating in spectral domain, such as SS regime using the output 1'.

FIG. 11 discloses an embodiment for full field TD low coherence gating applied to the CG-WFS. This is assembled around a full field TD-OCT system. In the reference arm, microscope objectives 14' and 14" compensate for the dispersion introduced by lens 14, like in any full field OCT, where the microscope objectives used in the reference and the object arm should be essentially similar. The scanning to explore the variation of aberrations with depth is performed by moving the stage 27. The stage 21 is fixed. By moving stage 27, the length of the object arm, 10 is varied, and in this way the OPD in the low coherence interferometer is adjusted to other positions in depth in the object 101. The focus position in the sample 101 also changes in synchronism, if the object 101 has an index of refraction of 1.4, as shown in the U.S. Pat. No. 7,330,273, A. Podoleanu, J. Rogers, "Compact high resolution imaging apparatus" and in the article: "Simplified dynamic focus method for time domain OCT", by M. Hughes and A. Gh. Podoleanu, published in Electronics Letters, Volume 45, Issue 12, Jun. 4, 2009, 623-624. The same solution can be used here for the CG-WFS to maintain in synchronism the coherence gate with the focus gate. The light in the object arm 10 is routed via mirrors 22$a'$ and 23$a'$ and focusing element 14, all supported by the translation stage 28. If the lenslet array 34 is removed, the set-up becomes a full field OCT system with dynamic focus. Therefore, two possible regimes of operation are possible: (i) aberrations evaluations, where 34 is in place like in FIG. 11 and (ii) OCT images acquisition, when the lenslet array 34 is removed. In the first stage, aberrations are collected and they can be used to inform correction via the corrector, 11, similar to embodiments in FIGS. 9 and 10. Then, under a fixed correction, images are collected in the second stage.

Alternatively, an extra imaging OCT channel is added, similar to embodiments in FIGS. 9 and 10, but photodetectors 42 and 42' are replaced by 2D arrays, CCD or CMOS, 33a and 33b) only one may suffice, for full field OCT). For MM operation, the receiver 60 is equipped with a 2D array, CCD or CMOS, 33c. Scanning in depth and focusing is performed at the same time by moving the translation stage 28. This avoids the complex mechanics required by flipping 34. For a given position of stage 28, aberrations from a given depth are acquired, using the CG-WFS, then corrections are applied and at the same time, imaging in the OCT channel, 40 and in the MM channel, 60, are performed. four gates are kept in synchronism if the index of refraction of the sample 101 is close to 1.4, focus and coherence gate in the CG-WFS 30 and focus and coherence gate in the OCT imaging channel, 40.

Other embodiments and alternative arrangements of WFSs, OCT, SLO, CM, MM which have been described above may occur to those skilled in the art, without departing from the spirit and scope of the appended claims. For those skilled in the art, it will be obvious that the same WFS method and devices here disclosed can be incorporated into apparatuses that could operate in transmission, such as for transmission microscopy, where the object 101 is a microscopy specimen and the object arm is suitably routed according to means known in the art to provide WFS information and imaging.

It should be also possible to use the depth resolved WFS in reflection and the imaging system in transmission and vice-versa.

The source 1 could be a spatial distribution of low coherent sources, for instance superluminiscent diodes or independent emitters, such as low coherence VECSELs. This eliminates the need of transversal scanning means 16 and 5. Each beamlet interferes with itself on subapertures of the array 33.

If a spatial light modulator (SLM) is used, then object beamlets and reference beamlets are generated which implement simultaneous low coherence gating for each output beam created. Again, sub-apertures are used out of the 2D camera 33.

In the same spirit, in order to implement swept source principle in the low coherence gating, the optical source 1' could be an array of swept sources, no need for an XY scanner and the interface optics transfers an array of spots to the eye 100 or to the lens in front of the object 101.

Other modifications and alterations may be used in the design and manufacture of the apparatus of the present invention without departing from the scope of the accompanying claims.

For instance, in some implementations, it may be desirable, in order to eliminate the speckle, that the light from the optical source is passed through a multimode fiber or other means for spatial scrambling of phase, such as a diffusing moving diffuser or a chopper.

For enhanced signal to noise ratio, it may be desirable that the optical source is pulsed and the camera 33, or cameras 33 and 33' are opened for a short time. The shorter the exposure time, less the washout of interference fringes due to target movement. This improves the interference signal. In such cases, the optical source 1, either broadband or narrow swept, 1', is pulsed synchronously with the camera 33 (or cameras 33 and 33') with a duration determined by its (their) exposure time. The optical pulse power can be increased up to the average power corresponding to the safety threshold. For instance, for a pulse width of 1 ms and frame rates of 200 Hz, which correspond to periods of 5 ms, the pulse power can be increased 5 times over the safety value.

In all embodiments where a lenslet array is used, to implement a Shack-Hartmann sensor, such lenslet array can be replaced with an array of holes, according to principles known in the art in connection to Hartmann masks and Hartmann sensors.

In all embodiments, where lenses are mentioned, curved mirrors are also possible to be used, such as parabolic or spherical.

We claim:

1. A method for depth resolved wavefront sensing of an optical beam reflected or transmitted by an object, the method comprising:
    using a first splitter to produce an incident optical object beam and a reference beam from an optical source,
    wherein the incident object beam is reflected or transmitted by the object to produce an emergent optical beam,
    producing multiple object beams by traversing a multiple beam device by exactly one of the emergent object beam, and the incident object beam, to produce multiple object beams from the emergent object beam, and sending the multiple object beams via a two-output second splitter, to a reading block,
    wherein the reference beam is routed via the second splitter towards the reading block, and
    where the reading block has several pixels in transversal section; and
    processing the interference on the pixels of the reading block between the multiple object beams and the reference beam to locate the lateral position of centroids of maxima of interference signal on the reading block for each beam in the set of multiple object beams versus the optical path difference measured as a difference of length between object path measured from the first splitter to the object and back to the second splitter, and reference path length, measured from the first splitter up to the second splitter.

2. A method according to claim 1 where the aberration information is the local tilt of the wavefront in points across the optical beam section from a direction perpendicular to the beam propagation direction.

3. A method for depth resolved wavefront sensing according to claim 1 wherein the wavefront sensing principle to sense uses laser ray tracing.

4. A method for depth resolved wavefront sensing according to claim 1 wherein the wavefront sensing principle to sense uses Shack-Hartmann wavefront sensing.

5. A method for depth resolved wavefront sensing according to claim 1 wherein the wavefront sensing principle to sense uses pyramid wavefront sensing.

6. A method for depth resolved wavefront sensing according to claim 1 wherein the optical source is broadband and the processing of the interference signal proceeds according to principles of phase shifting interferometry.

7. A method for depth resolved wavefront sensing according to claim 1 wherein the low coherence interferometry method is full field time domain optical coherence tomography using a smart array.

8. A method for depth resolved wavefront sensing according to claim 1 wherein the optical source is tunable and narrow band, and the processing of the interference signal proceeds according to principles of swept narrow band optical source.

9. A method for depth resolved wavefront sensing according to claim 1 where the multiple beam device is a lenslet array to produce multiple beams simultaneously.

10. A method for depth resolved wavefront sensing according to claim 1 where the multiple beam device is a pyramid to produce multiple beams simultaneously.

11. A method for depth resolved wavefront sensing according to claim 1 where the multiple beam device is a 2D scanning element to produce multiple beams sequentially.

12. An apparatus for depth resolved wavefront sensing comprising:
an optical source for producing an optical beam
a first splitter to produce an optical object beam and a reference beam from the optical beam, the object beam being directed to an object for being reflected or transmitted by the object to produce an emergent optical beam,
a multiple beam device in the path of exactly one of the emergent optical beam and the incident optical beam to produce multiple object beams from the emergent object beam,
a second two-output splitter for directing the multiple optical beams to a reading block consisting of several pixels in transversal section,
wherein the reference beam is routed via the second splitter onto the reading block, and
a processor to process the interference on the pixels of the reading block between the multiple object beams and the reference beam to locate the lateral position of centroids of maxima of interference signal on the reading block for each beam in the set of multiple object beams versus the optical path difference measured as a difference of length between object path measured from the first splitter to the object and back to the second splitter, and reference path length, measured from the first splitter up to the second splitter.

13. An apparatus for depth resolved wavefront sensing according to claim 12 where the reading block comprises a 2D photodetector array, illuminated by beams coming out from one of the outputs of the second splitter.

14. An apparatus for depth resolved wavefront sensing according to claim 12 wherein the reading block comprises two similar 2D photodetector arrays, each illuminated by one of the outputs of the second splitter, and a signal difference is created for each pixel of the reading block at its output, to implement balance detection to reduce the strength of non interference signals.

15. An apparatus for depth resolved wavefront sensing according to claim 13, where the 2D photodetector array is a CCD camera.

16. An apparatus for depth resolved wavefront sensing according to claim 13, where the 2D photodetector array is a CMOS camera.

17. An apparatus for depth resolved wavefront sensing according to claim 13, where the 2D photodetector array is a smart array, with parallel reading on each pixel.

18. An apparatus for depth resolved wavefront sensing according to claim 14, where the 2D photodetector arrays are similar CCD cameras.

19. An apparatus for depth resolved wavefront sensing according to claim 14, where the 2D photodetector arrays are similar CMOS cameras.

20. An apparatus for depth resolved wavefront sensing according to claim 14, where the 2D photodetector arrays are similar smart arrays, with parallel readings on each pixel.

21. An imaging apparatus for an object, where the imaging apparatus comprises:
an optical source for producing an optical beam
a first splitter to produce an optical object beam and a reference beam from the optical beam, the object beam being directed to an object for being reflected or transmitted by the object to produce an emergent optical beam,
a multiple beam device in the path of exactly one of the emergent optical beam and the incident optical beam to produce multiple object beams from the emergent object beam,
a second two-output splitter for directing the multiple optical beams to a reading block consisting of several pixels in transversal section,
wherein the reference beam is routed via the second splitter onto the reading block, and
a processor to process the interference on the pixels of the reading block between the multiple object beams and the reference beam to locate the lateral position of centroids of maxima of interference signal on the reading block for each beam in the set of multiple object beams versus the optical path difference measured as a difference of length between object path measured from the first splitter to the object and back to the second splitter, and reference path length, measured from the first splitter up to the second splitter,
wherein the imaging apparatus uses the information provided by the apparatus for depth resolved wavefront sensing to implement wavefront correction for the optical signal from the object in order to improve the quality of the image acquired from selected depths in the object.

* * * * *